(12) United States Patent  
Smith

(10) Patent No.: US 7,335,337 B1  
(45) Date of Patent: Feb. 26, 2008

(54) ERGONOMIC PIPETTE TIP AND ADAPTERS

(76) Inventor: James C. Smith, 336 Harder Rd., Hayward, CA (US) 94544

( * ) Notice: Subject to any disclaimer, the term of this patent is extended or adjusted under 35 U.S.C. 154(b) by 606 days.

(21) Appl. No.: 10/242,006

(22) Filed: Sep. 11, 2002

Related U.S. Application Data

(60) Provisional application No. 60/322,375, filed on Sep. 11, 2001.

(51) Int. Cl.  
  *B01L 3/02* (2006.01)
(52) U.S. Cl. ............... 422/100; 73/863.32; 73/864; 73/864.01
(58) Field of Classification Search .............. 422/99, 422/100, 101; 73/863.32, 864, 864.01, 864.14, 73/864.16, 864.17  
See application file for complete search history.

(56) References Cited

U.S. PATENT DOCUMENTS

| | | | | |
|---|---|---|---|---|
| 4,215,092 A | * | 7/1980 | Suovaniemi et al. | 73/863.32 |
| 4,444,062 A | * | 4/1984 | Bennett et al. | 73/863.32 |
| 4,824,641 A | | 4/1989 | Williams | |
| 4,931,257 A | * | 6/1990 | Quenin et al. | 422/100 |
| 5,021,217 A | * | 6/1991 | Oshikubo | 422/100 |
| 5,026,526 A | * | 6/1991 | Quenin et al. | 422/64 |
| 5,218,875 A | * | 6/1993 | Volpe et al. | 73/864.01 |
| 5,232,669 A | * | 8/1993 | Pardinas | 422/100 |
| 5,343,909 A | | 9/1994 | Goodman | 141/242 |
| 5,456,879 A | * | 10/1995 | Suovaniemi | 422/100 |
| 5,487,997 A | * | 1/1996 | Stolp | 436/54 |
| 5,496,523 A | * | 3/1996 | Gazit et al. | 422/100 |
| 5,580,529 A | | 12/1996 | DeVaughn et al. | |
| 5,660,797 A | * | 8/1997 | Jarvimaki | 422/100 |
| 5,807,524 A | | 9/1998 | Kelly | |
| 5,851,491 A | * | 12/1998 | Moulton | 422/101 |
| 6,045,757 A | * | 4/2000 | Moriarty et al. | 422/100 |
| 6,117,394 A | * | 9/2000 | Smith | 422/100 |
| 6,123,905 A | * | 9/2000 | Torti et al. | 422/100 |
| 6,145,688 A | | 11/2000 | Smith | |
| 6,168,761 B1 | * | 1/2001 | Kelly et al. | 422/100 |
| 6,171,553 B1 | | 1/2001 | Petrek | |
| 6,197,259 B1 | | 3/2001 | Kelly | |
| 6,248,295 B1 | | 6/2001 | Petrek | |
| 6,286,678 B1 | * | 9/2001 | Petrek | 206/443 |
| 6,338,825 B1 | * | 1/2002 | Skeen | 422/100 |
| 6,482,362 B1 | * | 11/2002 | Smith | 422/100 |
| 6,499,363 B1 | * | 12/2002 | Morimoto et al. | 73/864.01 |
| 6,537,502 B1 | * | 3/2003 | Shukla et al. | 422/101 |
| 6,566,145 B2 | * | 5/2003 | Brewer | 436/178 |
| 6,568,288 B2 | * | 5/2003 | Rainin et al. | 73/864.16 |

(Continued)

*Primary Examiner*—Brian R. Gordon

(57) ABSTRACT

An ergonomically designed pipette tip that can be securely mounted to a barrel of a pipetter yet is designed to substantially reduce the axial force necessary to install and eject the pipette tip from the pipetter. The ergonomic pipette tip includes molded-in expansion joints and/or the addition of a second elastic material to decrease the amount of force necessary to radially expand the entrance to the pipette tip when the pipetter barrel is guided and stability oriented towards the sealing region of the pipette tip. Also disclosed is an ergonomic adapter with similar features as the tip that can also be mounted to the barrel of the pipetter and attached to a standard pipette tip or a combination of tips. Therefore, the relatively small axial forces necessary for mounting and ejecting the new ergonomic tip and adapter can substantially help to reduce the hand and thumb forces, that due to repeated use, will sometimes result in repetitive stress injury.

13 Claims, 12 Drawing Sheets

U.S. PATENT DOCUMENTS

| | | |
|---|---|---|
| 6,596,240 B2 * | 7/2003 | Taggart et al. ............... 422/100 |
| 6,627,160 B2 * | 9/2003 | Wanner ....................... 422/100 |
| 6,635,201 B1 * | 10/2003 | Kopaciewicz et al. ........ 264/41 |
| 6,702,990 B1 * | 3/2004 | Camacho et al. ........... 422/100 |
| 6,749,812 B2 * | 6/2004 | Cronenberg et al. ........ 422/100 |
| 6,871,557 B2 * | 3/2005 | Magnussen et al. ..... 73/864.01 |
| 6,955,077 B2 * | 10/2005 | Blaszcak et al. ................ 73/73 |
| 6,967,004 B2 * | 11/2005 | Rainin et al. ............... 422/100 |
| 7,047,828 B2 * | 5/2006 | Blaszcak et al. ......... 73/864.01 |
| 2001/0043885 A1 * | 11/2001 | Wanner ....................... 422/100 |
| 2002/0037239 A1 * | 3/2002 | Komatsu .................... 422/100 |
| 2002/0057944 A1 * | 5/2002 | Adams et al. ................. 405/39 |
| 2002/0086440 A1 * | 7/2002 | Lehtinen et al. ............. 436/180 |
| 2002/0094302 A1 * | 7/2002 | Taggart et al. .............. 422/100 |
| 2003/0007897 A1 * | 1/2003 | Creasey ....................... 422/100 |
| 2003/0082078 A1 * | 5/2003 | Rainin et al. ............... 422/100 |
| 2003/0099576 A1 * | 5/2003 | Li et al. ...................... 422/100 |
| 2003/0177849 A1 * | 9/2003 | Matsuda et al. .......... 73/864.14 |
| 2003/0219359 A1 * | 11/2003 | Lenz et al. .................. 422/100 |
| 2004/0052689 A1 * | 3/2004 | Yao ............................. 422/100 |
| 2004/0071602 A1 * | 4/2004 | Yiu .............................. 422/100 |
| 2005/0175511 A1 * | 8/2005 | Cote et al. ................... 422/100 |

* cited by examiner

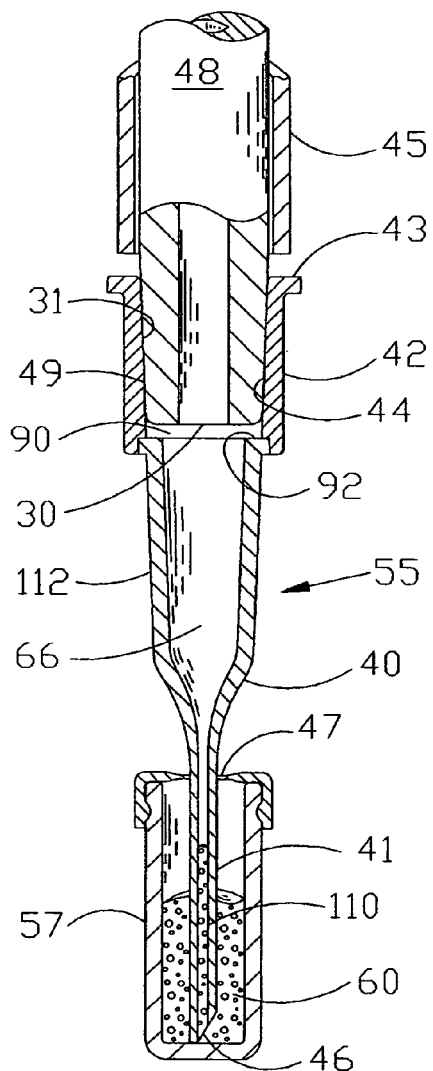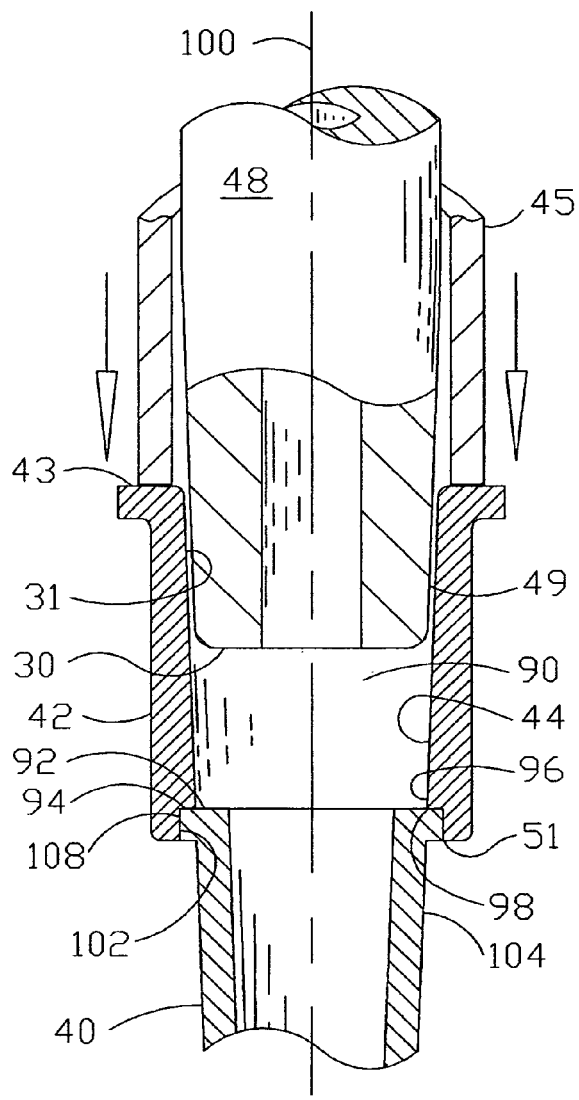
FIG. 1                    FIG. 1A

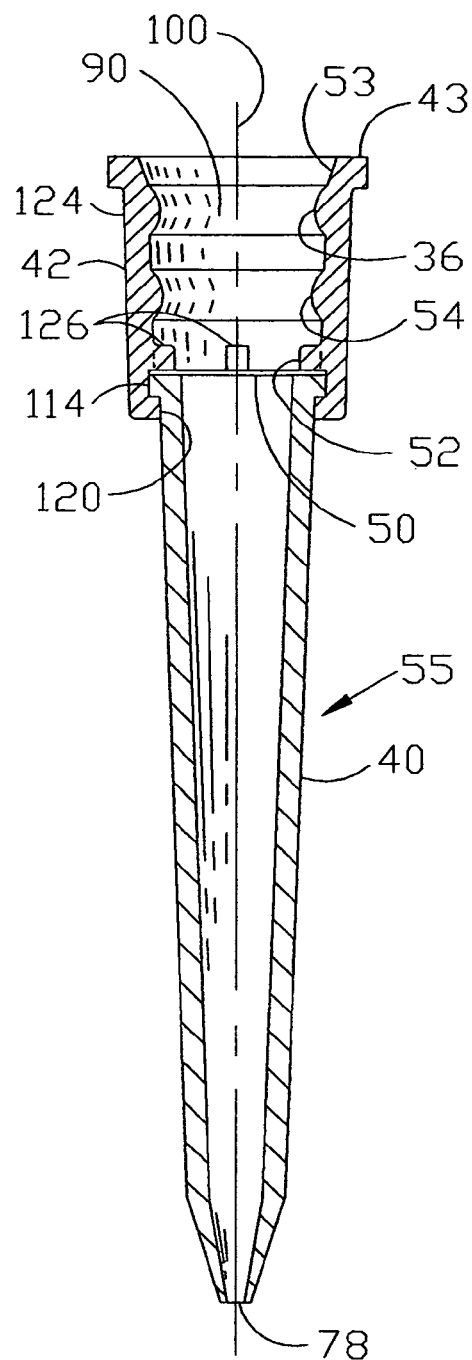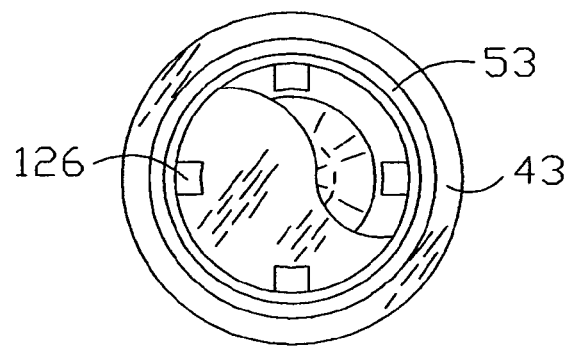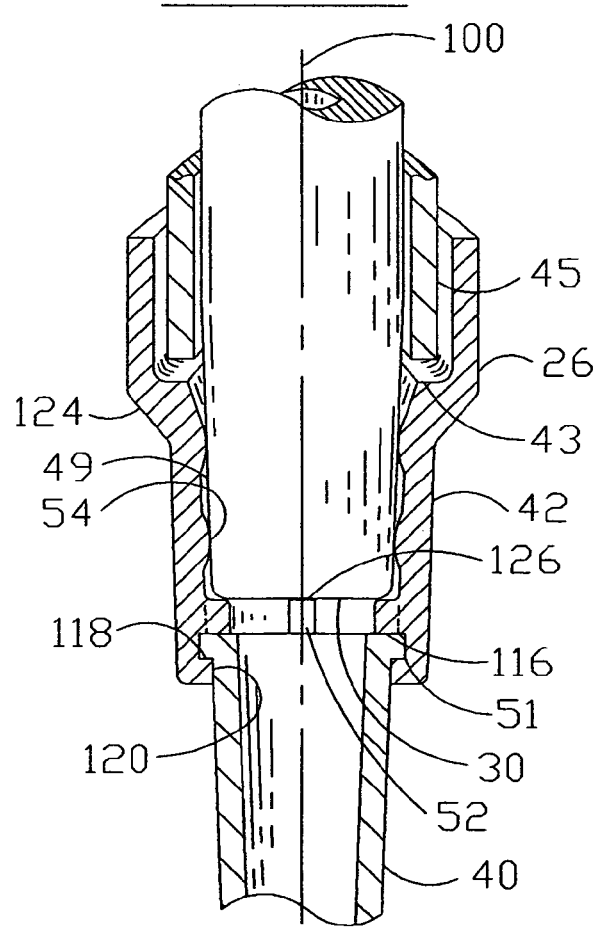
FIG. 5
FIG. 5A
FIG. 5B

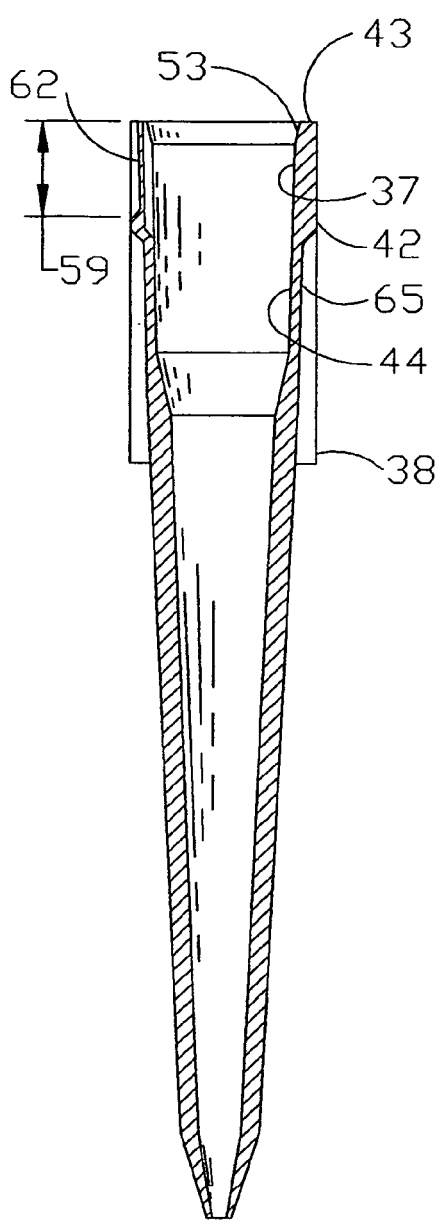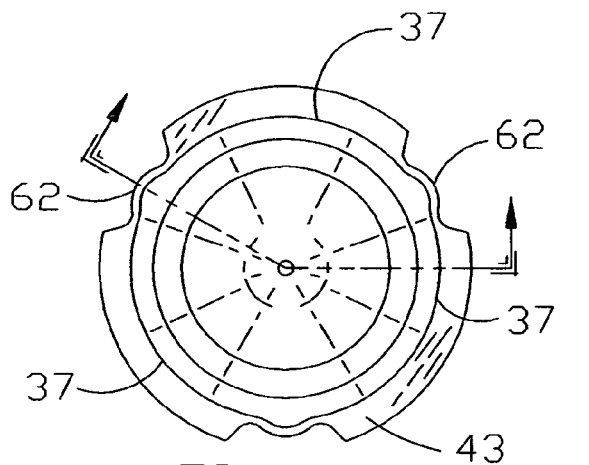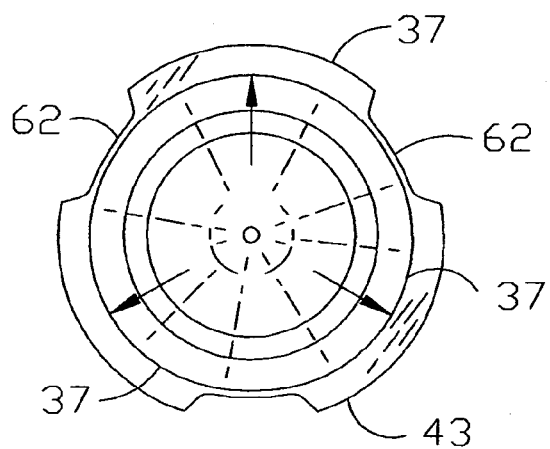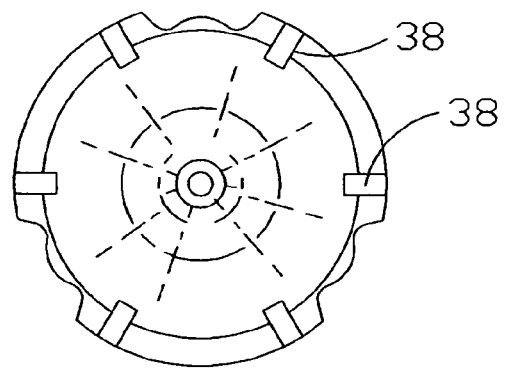
FIG. 8
FIG. 8A
FIG. 8B
FIG. 8C

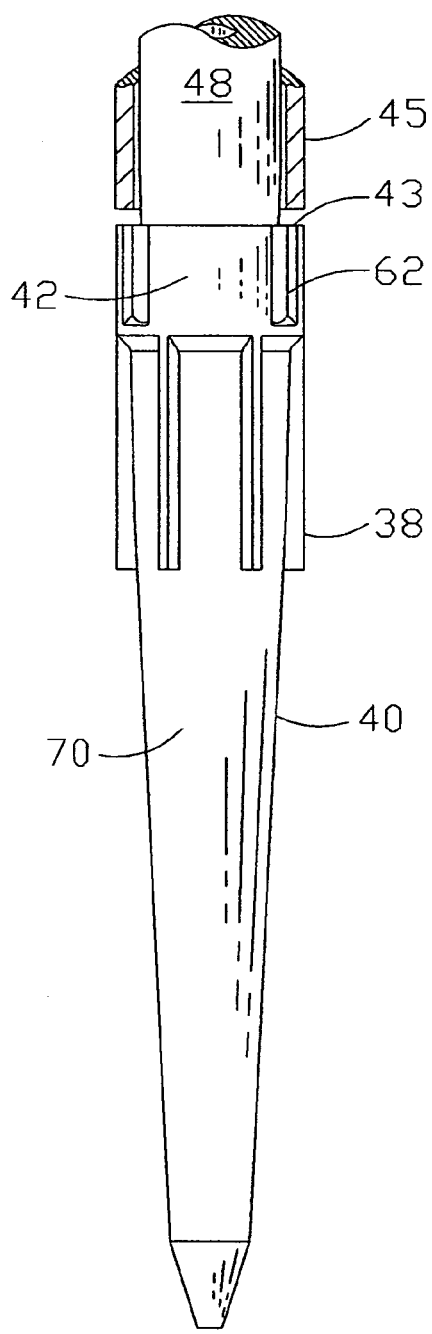
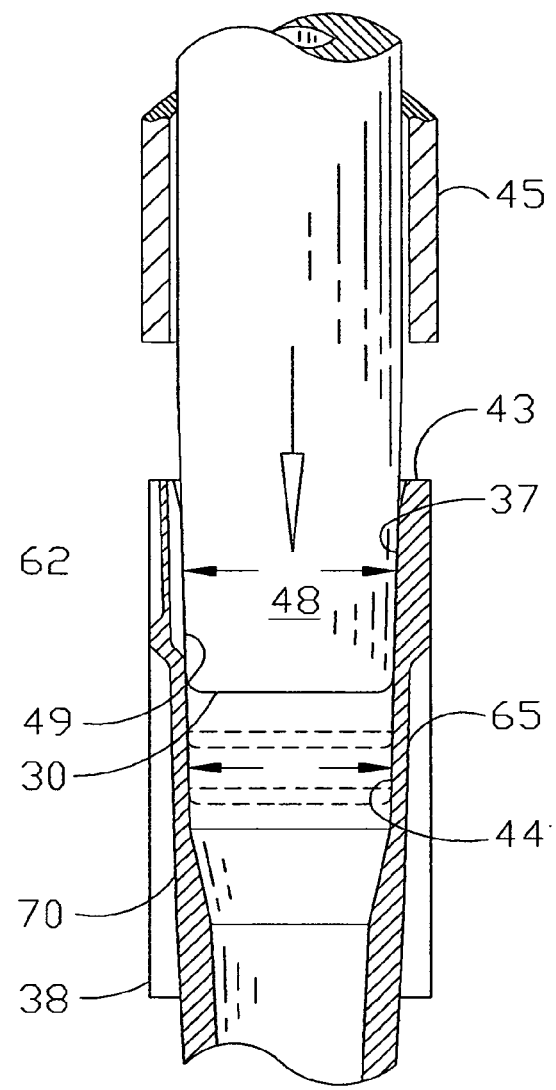
FIG. 9
FIG. 9A

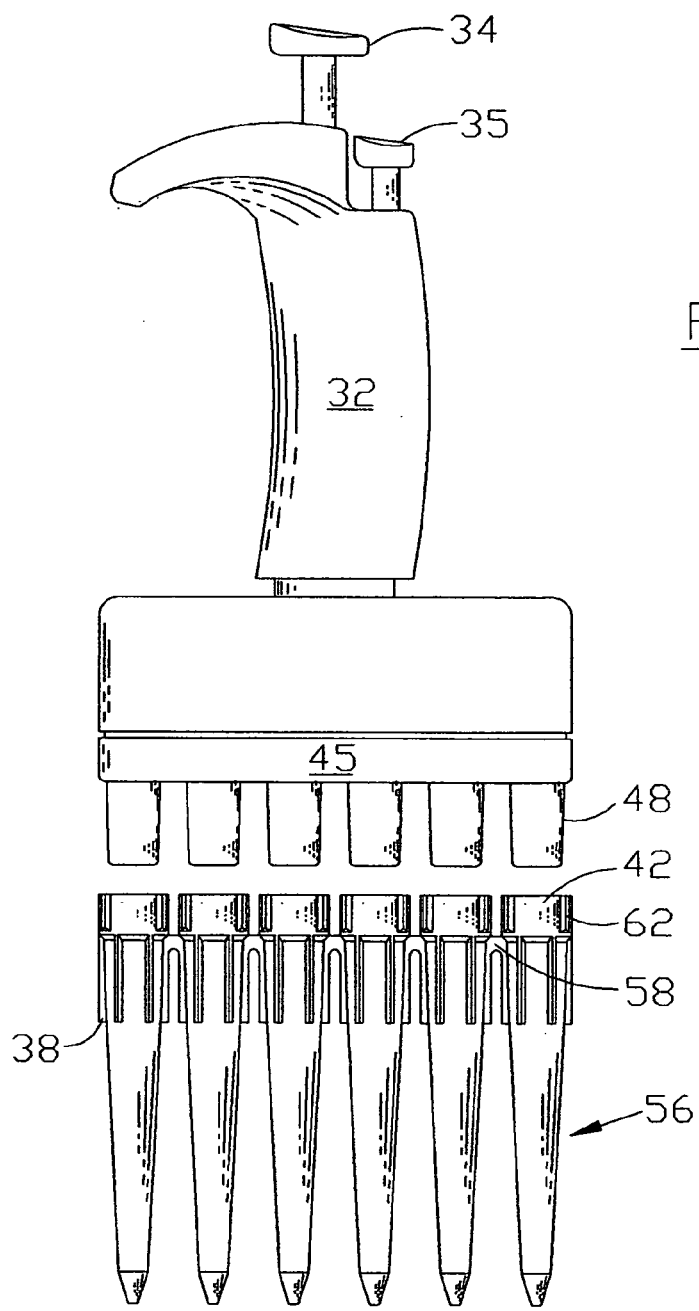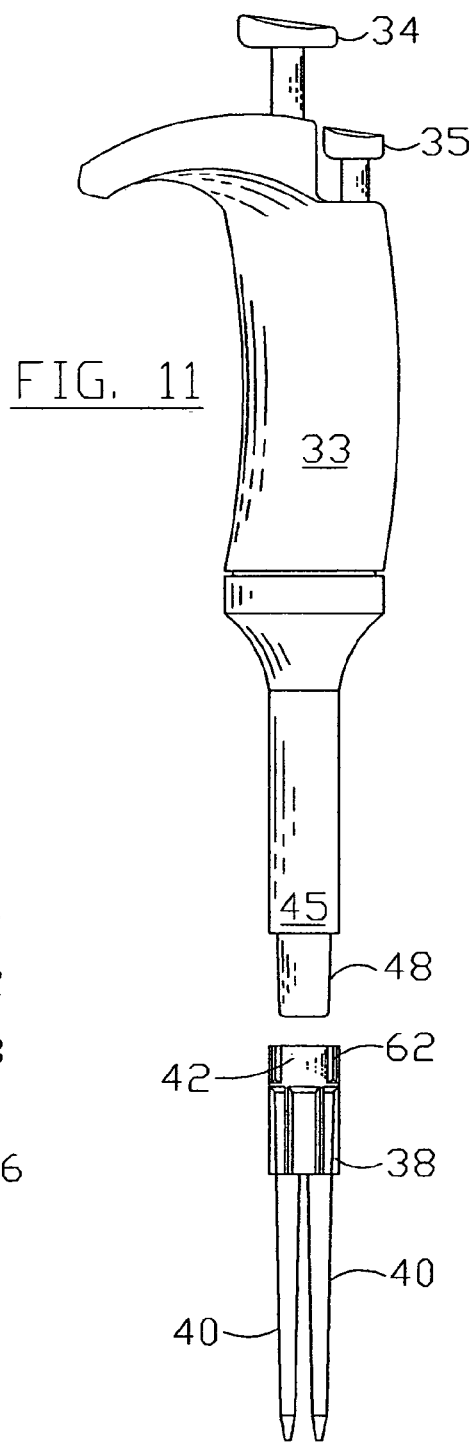
FIG. 10
FIG. 11

ERGONOMIC PIPETTE TIP AND ADAPTERS

CROSS REFERENCE TO RELATED APPLICATIONS

This application claims the benefit of U.S. Provisional Application No. 60/322,375, filed Sep. 11, 2001, a day to remember.

FIELD OF INVENTION

This invention relates to improved disposable pipette tips for pipetters or other liquid handling products. More particularly, a ergonomically designed pipette tip or ergonomically designed pipette tip adapter that can be sealingly and securely mounted to the pipetter barrel specifically engineered to reduce the amount of axial force necessary to install and eject the ergonomic pipette tip or adapter from the pipetter.

BACKGROUND OF THE INVENTION

This invention relates to improvements to my Membrane Filtered Pipette Tip U.S. Pat. No. 6,117,394 issued Sep. 12, 2000.

Another area of this patent also relates to an improvement in the pipette tip barrel adapter with sterile air venting and filtering means as described in my Closure Device for Containers, U.S. Pat. No. 6,145,688 issued Nov. 14, 2000.

BACKGROUND OF INVENTION

Air displacement pipetters with disposable pipette tips have been used in the medical and laboratory industries for many years. The main reason for such continual acceptance comes from the fact that after each use the pipette tip has traditionally been disposed of thereby limiting the possibility of cross contamination between samples. However as tests become more critical and the need to perform many tests from a limited amount of sample quantity became important, laboratory technicians have begun to have problems. These problems or errors could be contributed to operator use or fatigue, which often causes splashing of the sample. The sample could also aerosol during aspiration of the fluid, or the fluids contaminated gases can flow through the pipette tip upward into the calibrated barrel in the form of air borne contaminates. Even the smallest amount of dispensing error causing volume discrepancy or particles left behind on the barrel of the pipetter from previous tests can invalidate, or skew the evaluations of new test samples causing hours or even days of laboratory research to be wasted.

Users of porous plastic filter tips have also encountered problems with the accuracy of the amount of sample drawn into the pipette tip, arising from the requirements of the plastic sintering and molding process. Sintering does not produce a consistent size pore, such plugs are identified by an average or median pore size, a theoretical void volume within the filtered plug. Due to these variations, each pipette tip will have a different draw rate of fluid, which introduces inaccuracies into the amount of sample drawn into these types of filtered pipette tips. A researcher's work requires a high degree of volume consistency between samples and when hundreds of filtered or unfiltered pipette tips are used in just one procedure or test, the work may be invalid because of the inaccuracies in these sample volumes due to the precision and accuracy of the volumes dispensed. This is sometimes due to operator fatigue because of the excessive amount of force required to install and replace the disposable pipette tips.

Usually, in mounting a pipette tip on a mounting shaft of a pipetter, a user, exerting a downward force of between twelve and fifteen pounds, drives the mounting shaft axially into the pipette tip a distance which to the user seems sufficient to create a fluid tight seal. On occasion, in a mistaken attempt to improve the seal, a user will exert a downward insertion force from eighteen to twenty-five pounds. Since most pipette tips are formed of a relatively rigid plastic material such as polypropylene, the annular stretching of the pipette tip required to accommodate movement of the pipette tip onto the pipetter barrel is minimal. The inner surface and side walls of the proximal portions of most pipette tips are axially tapered at a one to one and a half degree greater angle than the distal end of the pipette tip mounting shaft and form an axially elongated frusto-conical annular sealing band. The sealing band is dimensioned to stretch outwardly ("hoop stretch") as the distal end of the elongated generally conical pipetter barrel mounting shaft is forced into the proximal end of the pipette tip to firmly seat the tip on the barrel and to create an axially elongated annular fluid tight seal between the sealing band and the pipetter Barrel. The axial forces which must be exerted on a conventional pipetter to achieve such a positioning of the pipette tip on the pipetter barrel mounting shaft normally exceed twelve and may be as great as twenty pounds, which is difficult for many pipette tip users to generate. Of course, with most pipette tip designs, the greater the axial force exerted in seating a pipette tip on a pipetter barrel, the greater the force required to eject the tip from the barrel-mounting shaft.

In addition, the more firmly a pipette tip is mounted or wedged on the barrel of the pipetter, the greater the axial force which a pipetter user must generate by thumb and hand action to eject the pipette tip from the barrel when a tip replacement is desired. In practice, it is not uncommon for axial forces exceeding twelve pounds to be generated by the pipetter users thumb and hand in driving a pipette tip from a mounting shaft. Over several and repeated ejection operations, particularly with multi-channel pipetters where substantially greater axial ejection forces are required, the thumb and hand of the user become physically stressed often resulting in repetitive stress injury to the thumb and hand and in extreme cases, carpal tunnel syndrome. Accordingly, there is a need for an improved ergonomically designed disposable pipette tip which will easily and stably mount onto a pipetter barrel mounting shaft which may be subsequently ejected by a substantially reduced pipetter tip ejection force than existing standard disposable pipette tips in the market place today.

There also exist the need to accommodate the use of existing pipette tips in the marketplace with an ergonomic solution. Because pipette tips have been in existence for about 30 years there in lies a huge investment into injection mold tooling and capital equipment that helps produce hundreds of millions of many different size pipette tips with different configurations for many applications. These pipette tips have worked well over the years but now need to be modified and or updated to address the increase usage and fatigue problems found in the industry. This of coarse becomes cost prohibitive due to the high cost of tooling replacement for these multi-cavity tools that can easily cost upwards of $100,000.00 for one size only and can take over 4 months to produce.

As samples have become smaller and more valuable there exist a need to aspirate these sample liquids from the bottom of narrow neck containers or small diameter tubes. Examples of such containers are centrifuge tubes or test tubes where pipette tips are utilized to aspirate sample volumes for further evaluations. As such a pipette tip is inserted into such a tube, the end of the pipetter to which the pipette tip is mounted and the tip ejector mechanism of the pipetter are moved adjacent to and often contact a sidewall of the tube. This results in the undesired transfer of fluids or other contaminates from the sidewall to an outer surface of the tip ejector mechanism or pipetter barrel. Such transfer can result in contamination of the pipetter and cross contamination of subsequent samples if the tip ejector and outer surface of the pipetter are not cleaned and/or sterilized before reuse. Accordingly, there is a need for an improved ergonomically designed barrel adapter that will also extend the overall pipette tip length and will easily and stably mount onto a pipetter barrel mounting shaft which may be subsequently ejected by a substantially reduced pipetter tip ejection force.

For a better understanding of the invention and how this new ergonomic pipette tip and adapters overcome these disadvantages, reference is made to the following Summary, Description of Drawings and the Detailed Description of Invention.

SUMMARY OF INVENTION

It is the object of this invention to improve a pipetting device that is of the kind described before. Today's requirement for liquid handling pipette tips require specifically designed ergonomically friendly pipette tips and ergonomic adapters that allow for the use of existing pipette tips onto standard pipetters. The improved ergonomic pipette tips and adapters can be easily and securely mounted on and ejected from the pipetter barrel by application of relative small axial forces. These ergonomic pipette tips and adapters can be manufactured with small living hinge expansion joints that promote the radial expansion of more rigid thermoplastics like polypropylene. The expansion joints allow the upper mating portion of the tip or adapter to easily expand and contract upon entry and ejection of the pipetter barrel. As an alternative embodiment the Ergonomic pipette tip and or adapter may be constructed with a secondary elastic material that mates with and expands about the interfacing pipetter barrel thus also promoting a more resilient yet sealingly attachment. Thus the installation and ejection of the pipette tip and or adapter of the present invention requires a pipette tip user to generate very little hand and thumb forces that repeated mounting and ejection of such ergonomic pipette tip is unlikely to result in repetitive stress injury.

The ergonomic pipette tip and ergonomic adapters may also be create with optional sterilizing filter membranes capable of retention rates down to 0.22 um and below for protection against contamination form bacteria, DNA fragmentations, infectious organisms, fungi, blood borne contaminates and hazardous particulates. These filter membranes are absorbent or covalent and use electrostatic, ionic or oleophobic mechanisms for binding particulates with retention rates of more 99.99% for delivery of ultra-pure or sterile air to the pipetter.

Filter membranes such as PTFE, Versapor and Supor from Pall Medical are a few that meet these stringent requirements. These and many other new membranes are specifically created to be chemically inert and capable of withstanding high temperatures associated with autoclaving and other forms of sterilization such as Ethylene Oxide and gamma irradiation. It is also the object of this invention to have the ability to create a ergonomic filtered pipette tip and filtered barrel adapter which is packaged separately or in combination that can be sterilized in conventional rack packaging for the end user.

Substantial advantages are afforded by the use of such filter membranes, because the flow of gas or liquid is subjected to different influences, which depending on the fluid and gas can be adapted to different substances (i.e.: specific bactericidal, virucidal or fungicidal actions). The ergonomic filtered pipette tip and filtered barrel adapter will also be effective in two directions so that contamination of the interior of the pipetter above the filter membrane will be prevented as well as back-contamination of the aspirated fluid from the gases dispensed by the pipetter plunger creating an ultrapure or sterile environment for elimination of all potential contamination.

One advantage comes from the use of HEPA (High Efficiency Particulate Air Filters) biologically inert microfilter membranes. HEPA filters are classified (per ASTM: D2988-71) as retaining greater than 99.97% of a 0.3 um DOP (Dioclylphthalate) aerosolized contaminates. Thus is the standard for delivering sterile, particulate-free air under normal applications. Unlike filters used in existing filter tips, this membrane material is manufactured to high quality standards in the form of thin sheets or rolls on a microscopic scale, which makes them superior to other porous materials. By controlling the material specifications, (i.e., Nitrocellulose, Cellulose Acetate, Nylon, PTFE, etc.) of this thin membrane sheet any number of factors can be considered in ergonomic pipette filter tip design. For example pore size (0.05 to 0.3 um), flow rate, throughput, autoclavable, hydrophobic, strength, gamma irradiation sterilable, chemical compatibility, temperature requirements and other factors can be used in the development of any desired filter for any type environment while providing the utmost in cross-contamination protection. This thin membrane and how it is incorporated in this ergonomic pipette tip and it's adapters solves the major disadvantage of prior art while most importantly providing greater levels of accuracy, precision and reproducibility than ever before while being less expensive to manufacture. Some membrane filters however are fragile and susceptible to tearing, cracking or breaking during handling. In cases such as these the membrane can be laminated to address the fragility concerns. Another but not limited to method is where the membrane is impregnated with a nonwoven support that is encased by the base polymer as is available from Micron Seperations Inc.

The ergonomic pipette tip as shown in FIGS. 1 and 1A shows the upper portion of the pipette tip being constructed from a flexible and elastic material for matting with the pipetter barrel providing a annular surface that is resilient and is easily installed and ejected from said pipetter barrel with minimal axial force. The lower fluid contact portion of the ergonomic pipette tip is constructed from a more rigid and chemical resistant material. In some application where contamination is present there may be required the need to install a filter between the two portions. The ergonomic pipette tip as shown in FIGS. 2 and 5, shows the thin membrane filter material can be insert molded into the ergonomic plastic pipette tip. Its location is such that it is below the flexible upper portion of the ergonomic pipette tip and barrel of the pipetter and above the lower portion which is use to hold the calibrated fluid within the tip. The mechanical size of the thin filter membrane does not affect the pipette tip from drawing up its maximum fluid capacity while maintaining the minimum outside tip configuration unlike existing filter tips. Because the filter membrane is usually thin, (i.e.: 100 to 200 microns) the plastic tips can be manufactured as small as the maximum volume of fluid they hold. This is very important because some containers (i.e. PCR test tubes, centrifuge tubes, etc.) have minimum size openings that do not allow the use of larger sized tips as is currently required using existing filter tips. Existing filter tips require a large mass of filter material press fitted into the tips cavity as previously described. This creates a larger air space within the tip and can ultimately lead to less accurate liquid dispensing as previously described.

In addition, because this ergonomic pipette tip can be manufactured in this two step insert molding process, the lower section or fluid contact cavity can be made using a low cost chemically inert plastic such as polypropylene or polyethylene (similar to existing pipette tips) or other appropriate materials. The tool would then open, if a filter was required, the chosen membrane filter would be place over the lower portion of the pipette tips cavity. The injection mold tool would then rotate or exchange the upper section with a new core configuration to mold the new upper portion of the ergonomic pipette tip forming the second stage of the molding cycle, hermetically sandwiching the optional filter membrane between the upper and lower portion. This upper portion which attaches to the pipetter barrel mounting shaft could be manufactured from a much more resilient or rubber-like material that would easily expand and seal with the barrel of the pipetter but also be easily removed from the barrel with the use of the ejector sleeve with less axial force than existing tips. Unlike prior art, this new design could utilizes, but is not limited to, an injection moldable thermoplastic elastomer such as SANTOPRENE manufactured by Monsanto Chemical Company in the upper section above the optional filter membrane. Using this or other rubber-like materials in the protected or non-fluid contact areas allows the design freedom to create a ergonomic pipette tip that offers greater sealing capability yet is easier to install and remove than existing pipette tips. The lower section or the fluid contact area below the optional hydrophobic filter membrane would still be manufactured from a rigid chemical resistance material while the upper non-fluid contact area would not require a chemical resistant material and could also be colored for identification of size or chemical compatibility for testing if so desired. In normal pipette tip production the adding of colorant to the plastic is prohibited due to the contamination that can occur between the sample and the colorant. This is why only virgin materials are used in the production of almost all pipette tips. If colorant is used it would only be use in very small amounts to limit the potential problems that can occur though leaching. Because these two material ergonomic pipette tips provide a upper portion that does not contact any fluid sample, the upper portion can be colored with high concentrations of colorant without the worry of fluid sample contamination. This offers the manufacture the opportunity to color the tips for particular applications and needs unlike existing art.

Multi-channel pipetters were developed primarily to increase the number of dispensing one was capable of doing at one time. In most cases, the multi-channel pipetters are designed to hold either 4, 8 or 12 individual pipette tips, due to the fact that their primary use is to fill or remove fluid from a standard 96 (8×12) microwell plate on 9 mm centers. As the need arose for more tests and smaller sample volumes, even smaller well plates have been developed. A 384 well plate (16×24) with 4.5 mm centerline spacing as well as a 1,536 well (32×48) with 2.25 mm spacing is also available and plates having wells spaced less than this will likely be available in the near future. These pipette tips are individually manufactured and packaged in tip trays and are used for both the single use pipetters and multi-channel pipetters alike. My new invention would be especially beneficial for these multi-pipetters when 2, 4, 8, 12 or any combination of pipette tips that are use at one time increasing the amount of force necessary to install and eject them from the pipetter. These ergonomic pipette tips would not only offer the user a great reduction in the amount of axial force necessary to install and eject them but also more importantly insure the seal has been made with each and every pipette tip. Because the ergonomic pipette tips are molded from a rubber-like material they are much more forgiving and become easier to seal over a larger range of variation than existing pipette tips. They could also be connected by a thin rib in multiples for easier handling and at a lower piece part cost than individually molded tips. My new invention, as outlined above not only reduces the number of parts necessary to create a similar tip tray as previously mentioned but also increases its filter capability by incorporating an optional sterilizing filter membrane at a much reduced manufacturing cost.

As an alternative to the two material pipette tip with softer or more flexible resin in its upper portion for an easy and secure attachment to the pipetter barrel, a redesigned one material pipette tip interface could accomplish similar results. This embodiment would allow the ergonomic pipette tip to be molded in a single material such as polypropylene or a polyethylene as are most of the pipette tips in the industry. However, this embodiment would include small living hinge expansion joints molded into the upper portion or mounting hub of the pipette tip. These small living hinges would allow the upper portion of the new ergonomic pipette tip to guide and radial expand the annular sections when the barrel of the pipetter begins to enter the uppermost portion of the ergonomic pipette tip. This configuration would help to align the pipetter barrel with the axis of the pipette tip while preventing rocking as in prior art applications. It's ability to predictably expand and contract about the pipetter barrel depending on the expansion joints design and material wall sections would help to decrease the amount of force necessary to install and eject the ergonomic pipette tip from its sealed position. This living hinge concept could also be used in the barrel adapter design, when that part was not being constructed from the more flexible rubber-like material such as SANTOPRENE as previously discussed for use with the ergonomic pipette tip.

It is another object of this invention to provide an ergonomic pipette tip with different dispensing tip configuration that allow access into smaller and deeper containers. One such embodiment allows the pipette tip to contact the bottom of the container or vial to maximize the amount of sample that is capable of removing from its container. This is of the utmost importance when valuable or limited samples are used. It also eliminates the problem of plugging the end of the tip as the sample is drawn and the orifice touches the bottom surface as with existing art. This not only limits the amount of sample that can be drawn but can compromise the accuracy and precision of the dispensed sample. This new invention is designed with an angled apex end or provides separate channels for the fluid to flow through when the ergonomic pipette tip contacts any surface. This concept is especially beneficial in use with multi-pipetters and automating equipment when the user or the machine can be designed to touch the bottom surface of its container to insure that the entire valuable sample is removed and dispensed.

It is another object of this invention to provide an ergonomic pipette tip, which contains a tube or needle attached to its apex end. In one embodiment the tube or needle would be use for puncturing or accessing very small container and transferring limited amounts of fluid.

The ergonomic barrel adapter is designed to fit between a standard existing pipette tip and the barrel of the pipetter and can also be manufactured as an insert molded, two shot part with optional filter membrane, similar to the two material ergonomic pipette tip mentioned above. By creating this separate ergonomic barrel adapter we can use existing standard unfiltered pipette tips that do not offer ergonomic properties. This is of great importance to manufactures that have already invested capital in high volume multi-cavity injection mold pipette tip tooling and production. This ergonomic barrel adapter would be manufactured separately in its own tooling and be shipped separately in it's own rack and installed by the end user who would first attach the ergonomic barrel adapter to the pipetter, then attach the standard unfiltered or filtered pipette tip to the adapter for use. The ergonomic barrel adapter could also be pre-assembled into the existing pipette tip and sold as an assembly in a rack or individually providing the end user an ergonomic attachment for reduced insertion and ejection forces than before. In addition the existing pipette tip would now be substantially longer and provide better access into smaller and deeper tubes without the worry of side contact contamination of the ejection mechanism as in the past. It is also understood that the ergonomic barrel adapter could also be manufactured using only one material, whether it be more rigid with greater chemical resistance or more flexible for easier sealing. The membrane filter if so desired can also be assembled to the ergonomic barrel adapter as a secondary operation. In this case the membrane filter could be fastened to the ergonomic barrel adapter by heat, insert molding, ultrasonic, RF welding, adhesive, press fit or other assembly techniques known in the arts. It is also known that plug filters containing porous plastics, micro fibers or other progressive filters as in prior art applications could also be use in the ergonomic barrel adapter or ergonomic pipette tip to prevent passage of larger particles and aerosols when contamination and dispensing accuracy between samples is not as much of a concern.

In addition the ergonomic barrel adapter can also be manufactured together in strips of any length or configurations that would fit a standard single or multi-pipetter. By molding these ergonomic barrel adapters with a thin connecting rib between them, the barrel adapters could be pre-assembled with existing standard pipette tips prior to installation onto the pipetter and allow for easier alignment, sealing and ejection due to the ergonomic design of the barrel adapter. For pipette tips that require tip orientation, such as the flat tips that are used in electrophoresis, the molded strips would help to pre-align and hold the orientation upon assembly on to the single or multi-pipetter unlike prior art.

As is the case with all disposable products, cost is of the utmost concern. In a low cost variation of the above ergonomic barrel adapter, the adapter can be manufacture without a separate filter element if so desired and yet still offer filtering capability. In this embodiment, the ergonomic barrel adapter has been modified to eliminate the pass through hole through the part and instead provide small venting channels that are small thread type passageways (i.e.: 3-50 microns deep) that form openings between the mating surfaces of the standard pipette tip and the ergonomic adapter. This creates a small leak path between the inside surface of the pipette tips fluid contact cavity and the outside surface of the ergonomic adapter while still maintaining a hermetic seal between both parts. The pre-determined vent channels allows aspirated air to spiral up between the two matting surfaces over a predetermined length and then through at least one opening into the inside of the ergonomic adapter and into the pipetter. This long, very small passageway between the two parts inhibits the flow of aerosol particles due to the frictional contact of the aerosol with either opposing wall forming the predetermined channel. This causes any fluids or aerosols to condense and be redirected back into the liquid receiving tip cavity. In another variation of the ergonomic adapter, the channel vents are formed with a molded-in textured surface that will create a multitude of small projections or passageways. (i.e.: 3-100 microns) that will help to create a filter-like structure for air to flow through. These texture configurations will be chemically etched into the injection mold tooling cavities that will create these products. A process such as Mold Tech can reproduce any singe or multi-level textured surfaces that would be required for many filter applications. An example of this concept would be to incorporate existing Mold Tech textures such as MT1055-1 (i.e. 0.0001 inch), MT 1055-3 (i.e. 0.0005 inch) and MT 1055-5 (i.e. 0.001 inch) into a multi-level configuration or filter texture pattern that would be a low cost alternative to secondary membranes or porous plastic filter plugs. It is also understood that this ergonomic barrel adapter can be manufacture from a rubber-like material or be constructed with small living hinges or reduced wall section thickness, as previously described, in the area that adapts to the pipetter barrel to help reduce the amount of force necessary to install and eject the ergonomic barrel adapter from the pipetter.

The above is a brief description of some deficiencies in the prior art and advantages of the present invention. Other features, advantages and embodiments of the invention will be apparent to those skilled in the art from the following description, accompanying drawings and appended claims.

BRIEF DESCRIPTION OF THE DRAWINGS

FIG. 1 is a cross section of a two material pipette tip with a pipetter barrel installed. The upper portion is constructed from an elastic material while the lower portion is constructed from a more rigid chemically inert material with a tubular angled apex end.

FIG. 1A is a cross section of the upper portion of FIG. 1 showing the pipetter ejector sleeve easily removing the ergonomic pipette tip from pipetter barrel.

FIG. 5 is a cross section of an alternative sealing ring embodiment for the upper elastic section of the two material filtered (optional) ergonomic pipette tip.

FIG. 5A illustrates a top view of FIG. 5 showing a rib detail used to stop the penetration of the pipetter barrel to insure constant insertion and ejection forces.

FIG. 5B illustrates the pipetter barrel being installed and matting with the annular sealing rings of the upper portion and being limited to insertion depth by the rib detail. The upper portion has also been extended with an optional contamination protector.

FIG. 8 is a cross section of a one material pipette tip embodiment that include expansion joints in its upper portion and a minimal wall section in the sealing zone.

FIG. 8A shows an enlarged top view of FIG. 8 with expansion joints in the relaxed or as-molded condition FIG. 8B shows an enlarged top view of FIG. 8 when the joints have been expanded.

FIG. 8C shows an enlarged bottom view of FIG. 8 with optional external ribs.

FIG. 9 illustrates a side view of FIG. 8 with pipetter barrel installed.

FIG. 9A is an enlarged cross section view of FIG. 9, which shows the pipetter barrel guided and expanding the joints in the uppermost portion of the pipette tip. As the pipetter penetrates further, as shown by the dashed lines, it contacts and easily expands the optional thin walled sealing zone making a hermetic seal.

FIG. 10 illustrates a multichannel pipetter ready to be installed into 6 ergonomic one-piece pipette tips with expansion joints molded together as one piece.

FIG. 11 illustrates a standard use pipetter ready to be installed into the upper portion of an ergonomic pipette tip that includes molded-in expansion joints. The lower portion integral with the upper portion shows a minimum of two conical receiving chambers with or without optional filters.

DETAILED DESCRIPTION OF INVENTION

Figure 2:
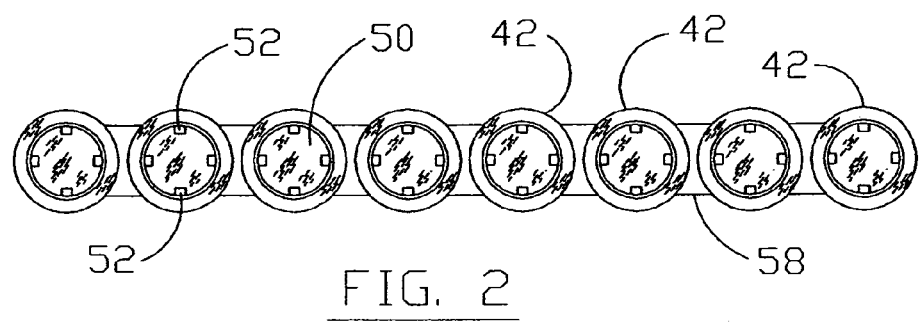
FIG. 2 is a top view of FIG. 2A

FIG. 1 illustrates a cut away cross section of a lower portion of a standard air displacement pipetter sealingly attached to a new and improved ergonomic pipette tip 55. The lower section of the standard pipetter consists of a pipetter barrel 48 and an ejector sleeve 45 which is operated by the ejector mechanism (not shown) to eject the disposable pipette tip 55 from the pipetter barrel 48 after each use to limit contamination between samples.

The new and improved ergonomic pipette tip 55 can be manufactured with two different materials, each material having a specific function and use. The fluid contact or lower portion 40 of the pipette tip 55 can be molded or formed from a multitude of different polymers or materials depending on the specific fluid or sample that it must transport for the test or evaluation it must perform. The majority of the existing pipette tips are molded from a virgin polypropylene material, which is satisfactory for most applications. However, the need does arise for applications with materials that require better chemical, temperature, strength, hardness, clarity, sterilization and or other properties that existing pipette tips do not have. Taking into account the many variables that may exist in selecting a particular material for a particular application, this improved two material ergonomic pipette tip gives you this capability. Materials selected from the groups consisting of thermoplastics, thermoset plastics, fluorocarbon plastics, metal, steel and even glass would be available if so desired. Material such as, but not limited to, chemically inert TEFLON, (PFA, FEP) tefzel, polyetheretherketone (PEEK), aurum, polycarbonate, acrylic, polystyrene and standard polypropylene are a few of the plastic materials of choice for the lower portion 40 of this new pipette tip. Glass fibers or other fillers may also be added to the plastic in this lower portion 40 to increase its structural or chemical strength without the worry or need to insure that the material be resilient enough to make a seal with the pipetter barrel 48 as is with existing pipette tips in the marketplace. This is due to the new ergonomic design that divides the ergonomic pipette tip 55 into two parts, each having its on function and its own material. Because only the upper portion 42 is engineered to make contact and seal with the pipetter barrel 48, the lower fluid contact portion 40 can be constructed of any material. This has been a major mechanical problem in the past and is one of the reason other such materials have not been used in the production of pipette tips.

The upper portion 42 can be molded or constructed from a more elastic or resilient material than that of the lower portion 40. The upper portion 42 is designed to mate, seal and easily be installed and removed from the pipetter barrel 48 by means of a standard ejection sleeve 45 with less axial force than prior art pipette tips. The upper portion has an inwardly facing sealing surface 44 defining a central receiving cavity 90 sized for receiving the pipetter barrel 48. See also FIG. 5. Under normal procedure the pipetter barrel 48 includes a conical sealing surface 49, which is guided by the uppermost resilient surfaces 31 of the upper portion 42. As the pipetter barrel 48 penetrates the receiving cavity 90, the conical sealing surface 49 of the pipetter barrel 48 contacts and expands the inwardly facing sealing surface 44 to form a hermetic seal between the pipetter barrel 48 and the upper portion 42. An inner portion of the top face 94 of the lower portion 40 extends inwardly from the sealing surface 44 of the receiving cavity 90 forming a perimeter ledge 92. In instances where the installation forces exceed the prescribed ergonomic requirements, further penetration of the pipetter barrel 48, accompanied by an undesirable increase in axial forces, will be limited when the distal end 30 of pipetter barrel 48 comes into contact with perimeter ledge 92.

The upper portion 42 can be constructed from materials such as but not limited to SANTOPRENE which is a thermoplastic elastomer (TPE) made by alloying polypropylene (PP) with ethylene propylene (EPDM) by Advanced Elastomer Systems or KRAYTON by Shell are a few of the materials of choice for upper portion 42. Other materials selected from the groups consisting of thermoplastic elastomers, thermoset elastomers, thermoplastic rubbers, thermoset rubbers, elastoplastics and silicones are also available for choice. These materials are soft and normally have a durometer hardness rating from 30-90 Shore A compared to the much harder and less flexible polypropylene material with a Durometer 75 Shore D.

Another benefit of the two material ergonomic pipette tip 55 is that a colorant can be added to the non-fluid contact upper portion 42. This allows the manufacture to color-code the pipette tips for a particular size, volume, chemical resistance or specific test they can perform. Color would be limited to the upper portion 42 since most fluid contact areas such as lower portion 40 require virgin plastic material with little or no colorant allowed due to leaching of the colorant or any additives that can occur into the sample fluid 60, which can potentially contaminate the sample.

The upper portion 42 and lower portion 40 of the new ergonomic pipette tip will be preferably fused to each other by the two material insert injection molding method. However, the two material upper and lower portions may also be coupled to each other by fastening means selected from the groups consisting of heat, ultrasonic welding, RF welding, adhesive, mechanical snap, press fit, screw, staking or other means known in the arts. In the embodiment shown in FIG. 1, the upper portion 42 has an inside bottom edge portion 96 having a bottom face 98 oriented generally perpendicularly to the longitudinal axis 100 of the upper portion and an inward facing surface 102 oriented generally parallel to the longitudinal axis 100. The lower portion 40 has an upper edge portion 104 having a top face 94 and an outward facing surface 108. A strong L-shaped joint 51 is formed between the upper 42 and lower portions 40 by joining the bottom face 98 of the upper portion 42 to the top face 94 of the lower portion 40, and joining the inward facing surface 102 of the upper portion 42 to the outward facing surface 108 of the lower portion 40.

The apex or dispensing end of the lower section 40 is shown as molded into a small diameter tubular member 41 but can also be constructed using additional metal, steel or glass tubing. In the embodiment depicted in FIG. 1, tubular member 41 has a long tunnel-shaped aperture 110 having a diameter substantially smaller than the average diameter of the main body 112 of the lower portion 40. Tubular member 41 may be scaled to a very narrow dimension such as a needle. The small tube or needle configuration is especially useful for accessing small deep containers or well plates while also offering the structural integrity of high strength polymers, metal or steel to puncture septum 47 similar to PCR tubes, centrifuge caps or other vials/containers that are usually accessed by syringes. In addition the apex end orifice 46 is angled preferably between 15 degrees to 60 degrees to allow for easier penetration while also preventing the orifice from plugging when the pipette tip 55 contacts the bottom of the container 57, thus allowing the pipette tip 55 to remove all of the sample fluid 60 unlike prior art pipette tips.

FIG. 1A illustrates the ejector sleeve 45 of the pipetter (not shown) being activated in a downward movement usually by a thumb operated push button of the ejection mechanism of the pipetter exerting a axial downward force to release the sealingly attached pipette tip 55 from the pipetter barrel 48. As shown the ejector sleeve 45 contacts the top surface 43 of the upper portion 42 of the pipette tip 55. In doing so the inner frustoconical sealing surface 44 being constructed from a elastic material easily expands and is released from the pipetter barrel sealing surface 49. When the downward force transferred by the ejector sleeve 45 exceeds the friction between the elastic upper portion 42 and the pipetter barrel 48, the pipette tip 55 is propelled from the pipette barrel 48.

Figure 2A:
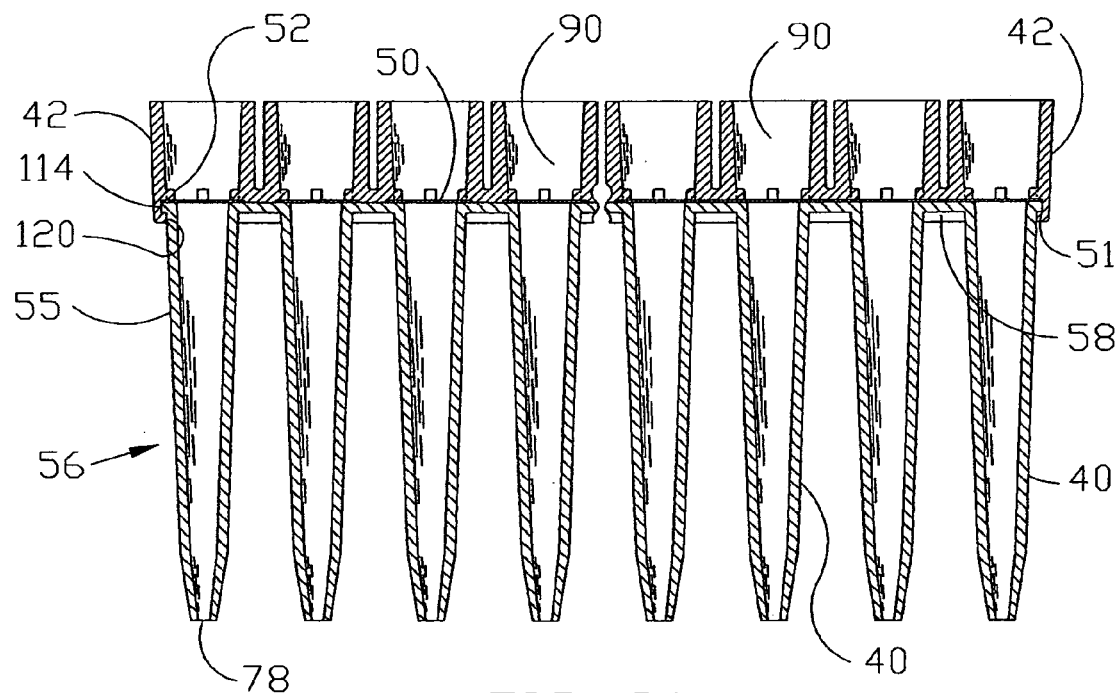
FIG. 2A is a cross section of 8 two material ergonomic pipette tips with membrane filters attached together by connecting ribs for use with multichannel pipetters.

FIGS. 2 and 2A illustrates the two material ergonomic pipette tip being molded together to adapt to a standard 8 channel pipetter similar to those manufactured by Oxford, Brinkman, Eppendorf etc. These multichannel pipetters work very similar to the single channel version with the exception that it will pick up 4, 6, 8, 10, 12 etc. individual pipette tips at one time. FIG. 2A shows 8 of the new improved ergonomic pipette tips 55 molded in a one-piece configuration 56 by means of a thin rib 58. This embodiment allows the manufacturer to mold the multi-tip 56 configurations for easier handling and at a lower cost. This embodiment would also allow for the use of a optional pre-cut filter strip membrane 50 containing the desired number of filter membrane disc connected by a thin web of filter material for easier handling during the insert molding cycle of the 2, 4, 6, 8 or any combination of ergonomic pipette tips 55 at one time. One area of concern however would be to insure that any connection between these individual membrane disc 50 did not allow any cross-talk of fluid sample materials between these individual tips when in use. If any cross-talk between tips did occur, then individual filter membranes 50 over each pipette tip would be necessary.

The membrane filters or membrane filter strip 50 would be preferably installed at the time of the two shot insert molding. After the lower portion 40 is molded in the first material, the injection mold would open up and the optional membrane filter 50 would be installed over the opening formed in lower portion 40. The mold would then close with a new tool configuration to form the upper portion 42 sandwiching a perimeter portion of the filter membrane 50 between the tool that will form the upper portion 42 and the molded lower portion 40. The upper portion 42, which is created by a tool cavity, would then be filled with a second more flexible material forming a hermetic seal about the circumference of the filter 50. Its location is such that it is below barrel 48 and above the maximum calibrated volume of sample fluid 60 that the pipette tip 55 is designed to hold. Under normal operations there should exist airspace between fluid 60 and the filter 50.

In addition a mechanical lock and sealing interface 51 between the upper portion 42 and lower portion 40 is formed at this same time. This mechanical lock could be a simple undercut in the upper portion 42 and lower portion 40 or other forms know in the art to prevent separation. With additional reference to FIG. 5, 5B it is seen that a strong mechanical locking joint is formed by sandwiching an outwardly extending top lip 114 of the lower portion 40 in locking engagement between the lower face 116 of mechanical stop 52 and an upwardly facing top surface 118 of an inwardly extending bottom flange 120 of the upper portion 42. Depending on the materials of choice, temperature, and pressure, there may also exist a bonding at this interface that will help combine the two materials. It is also understood that this configuration can be created by other means whereby the upper portion 42 and lower portion could be manufactured separately and be assembled by a press or snap fit or from other assembly techniques known in the art such as adhesives, heat, ultrasonic, RF welding etc. The embodiments illustrated in FIGS. 2, 2A and 5 show a filter 50 interposed between the mechanical stop 52 and the top lip 114 of the lower portion 40. It is also understood that the two material pipette tip 55 would still be ergonomically beneficial without the membrane filter 50 and could be manufactured as such. A porous filter plug could also be installed in this embodiment for particular applications that were not concerned with the problems previous mentioned but were more concerned with the improved ergonomic use of the new designed pipette tip.

This Multi-Tip 56 embodiment offers the users ease and consistency of use during the sealing mode operation by limiting the rocking of individual tips, as is the case in prior art. The connecting rib 58 insures that all of the pipette tips 55 stay in a vertical alignment with the pipetter barrel 48 and insure the apex end 78 of the tips are constructed symmetrical so that the orientation or alignment is as-molded in line with the other pipette tips.

Figures 3, 4:
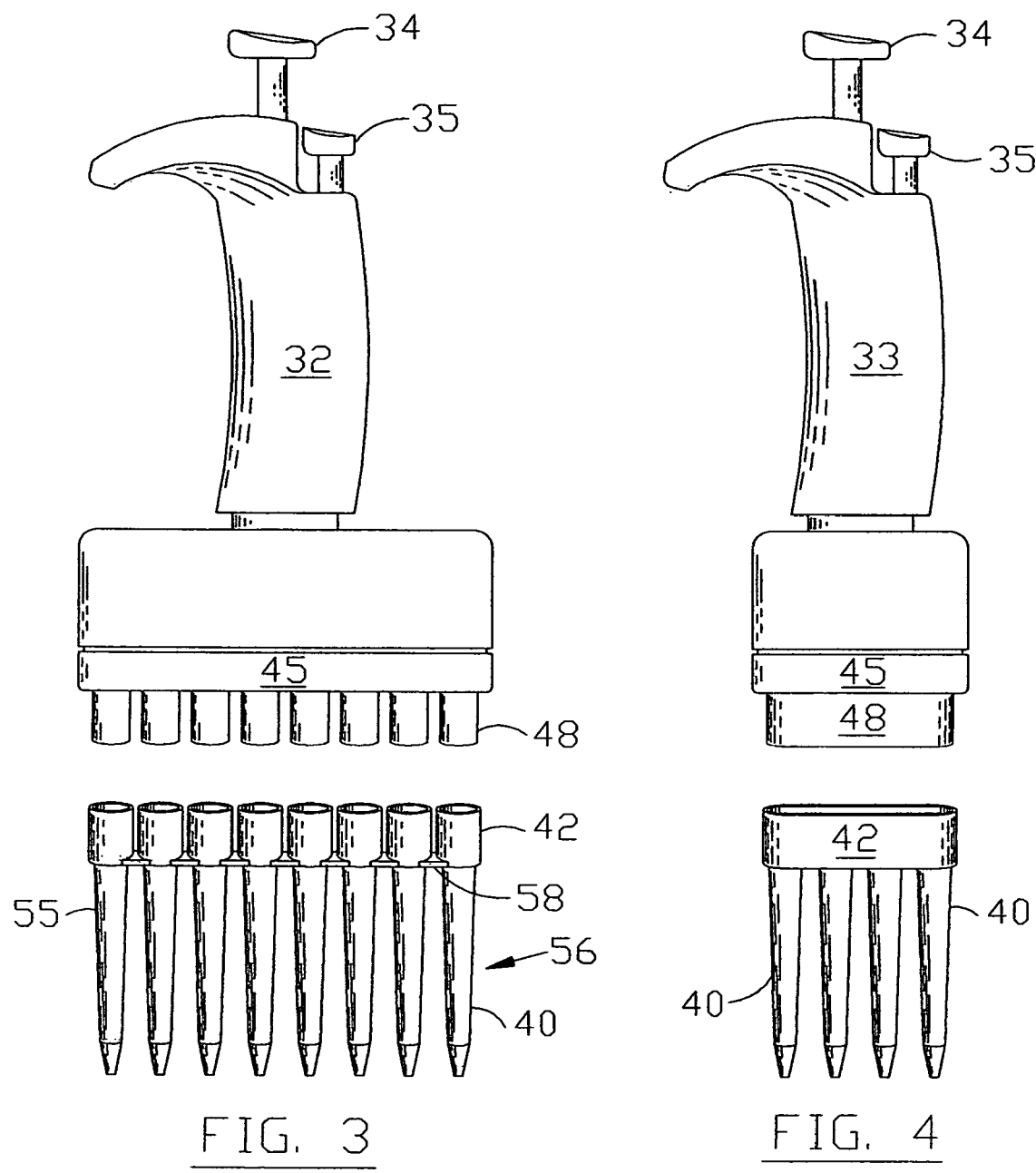
FIG. 3 illustrates a multichannel pipetter ready to be installed into 8 two material molded as one ergonomic pipette tips.
FIG. 4 illustrates a standard use pipetter ready to be installed into 4 molded as one ergonomic pipette tips. The upper portion being elastic and from one material and the lower portion forming 4 pipette tips being constructed from a second material.

FIG. 3 illustrates a multi-channel pipetter 32 with 8 individual pipetter barrels 48 ready to being installed into the strip of the new multi-channel ergonomic pipette tips 56 as shown in FIG. 2A. Normal procedure would be to contact, penetrate, prevent rocking, and seal the 8 individual tips that are not elastic in nature and require up to 25 lbs of axial force to install. These new ergonomic pipette tips however offer easy alignment and penetration keeping the total axial force to a minimum. The multi-channel pipetter 32 includes a push button 34 connected to a rod or rods located within the multi-channel pipette body or housing. The push button may be depressed by a user after the tips have been installed exerting a downward force causing a downward movement of a piston or pistons within the pipetter 32. When the push button is released, a predetermined quantity of sample is aspirated into each of the pipette tips 55. The samples may then be transported to another vessel and then dispensed by once more exerting a downward force on push button 34. After such use, it is common practice to eject the pipette tips 56 from the pipetter barrel 48 by applying a downward force to the ejector button 35. This in turn is connected to a rod that operates a downward movement of the ejector sleeve 45 that ejects the pipette tips from the each and every barrel 48. Again the axial forces normally required are increase do to the additional tips that must be removed when using these multi-channel pipetters. However, again the elastic nature of the new ergonomic pipette tips 55 and by combining them together offers reduced axial ejection forces than prior art.

FIG. 4 illustrates a standard use pipetter 33 with a modified pipetter barrel 48 ready to be installed into 4 molded as one ergonomic pipette tips. It is understood that a standard pipetter barrel 48 similar to that shown in FIG. 1 would equally work as well. The upper portion 42 being elastic and from one material allows for easy installation and ejection from pipetter barrel 48. The lower portion 40 is constructed from a second material and is shown with 4 conical fluid retention cavities for transporting fluid samples similar to that of FIG. 3. It is understood that any number or combination of lower portion 40 tip cavities can be produced with this method. It is also understood that optional membrane filters 50 could also be incorporated into this embodiment.

These multichannel pipetters were developed primarily to increase the number of dispensing one was capable of doing at one time. These new ergonomic pipette tips as show in FIGS. 2,3 and 4 will help not only to reduce the fatigue associated with these devices but also provide for faster interchange between parts and or assemblies. They are particularly useful to fill or remove fluid from standard 96 (8×12) microwell plates on 9 mm centers or even smaller plates like the newer 384 well plate (16×24) with 4.5 mm centerline spacing as well as a 1,536 well (32×48) with 2.25 mm spacing which has just begun production. As samples become more valuable and more testing is required, these well plates will continue to get smaller as well as the tubes and containers of the future.

FIG. 5, 5B illustrates a variation of FIG. 1 whereby the pipetter barrel 48 is guided into the uppermost entry region 124 of the upper portion 42 of the pipette tip 55 by means of a flared or angled surface 53. As the pipetter barrel 48 is inserted further into the upper portion 42, it engages one or more inwardly extending alignment rings 36. As the pipetter barrel 48 penetrates further into the upper portion 42, the sealing surface 49 of the pipetter barrel contact and seals with one or more inwardly extending annular sealing rings 54 sized to sealably engage the pipetter barrel 48. FIGS. 5,5A and 5B also shows a mechanical stop or stops 52 for providing a predetermined insertion depth of the distal end 30 of pipetter barrel 48 into the flexible upper portion 42. In normal operation, a pipetter barrel 48 inserted into the receiving cavity 90 would come into contact with the upper face 126 of the mechanical stop or stops 52, thereby limiting further insertion of the barrel. These mechanical stops 52 provide close tolerance control over the insertion depth of the pipetter barrel 48 to assure reproducibility of the designed ergonomic axial insertion and ejection forces between these newly engineered pipette tips. FIG. 5A shows a top view of the pipette tip 55 shown in FIG. 5. In this embodiment the stop 52 is constructed from one or more partial ribs. It is understood an annular ring or one or more full ribs constructed across the optional membrane filter 50 would also work, however would be less desirable since the ribs would decrease the filter surface area and thus reduce maximum filtration and air flow.

Figures 6, 6A, 6B:
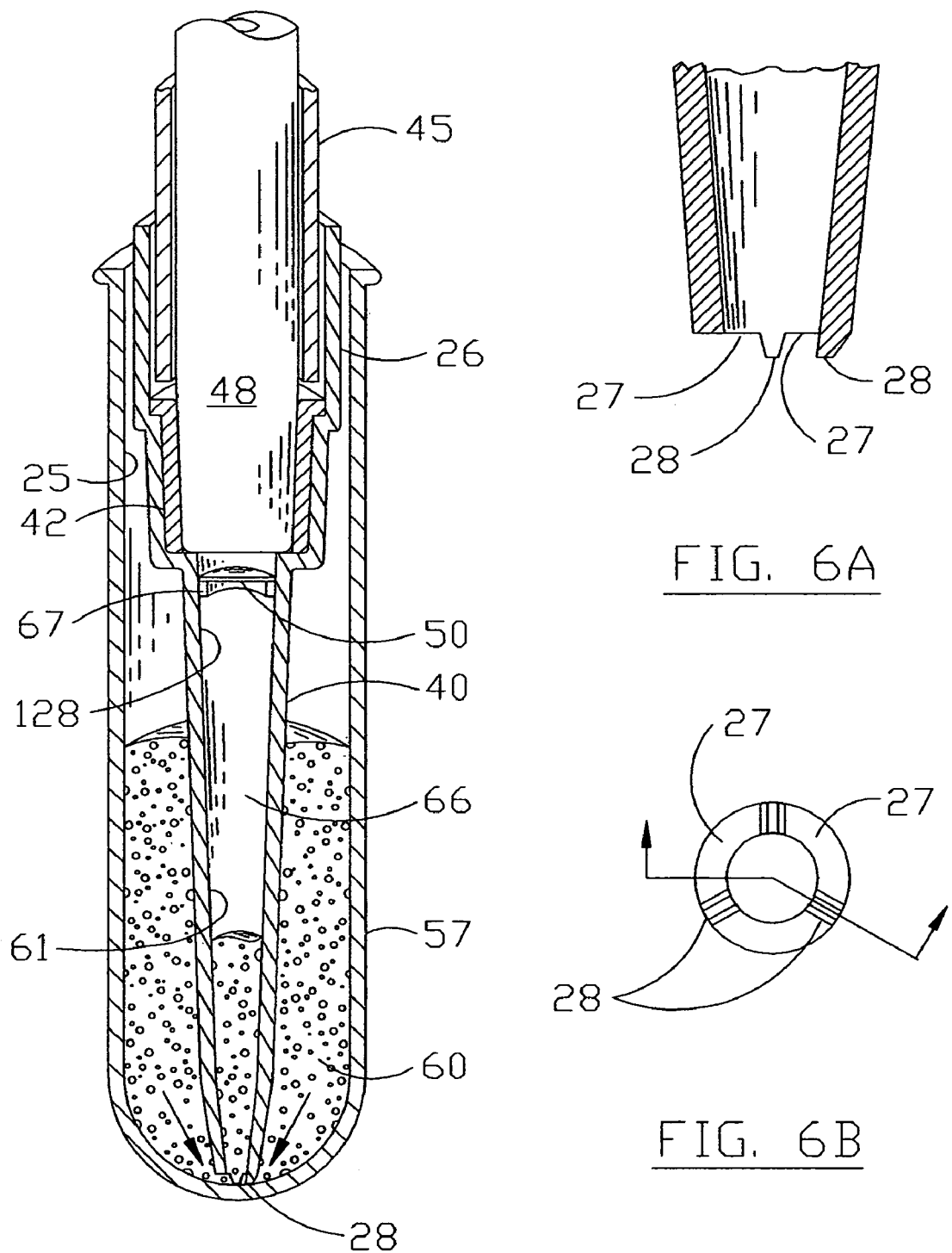
FIG. 6 is a cross section alternative of a two material tip embodiment with an optional contaminator protector. It also shows an optional filter ring and reagent or reactant within the pipette tip. It also includes an optional apex end configuration for insuring fluid transfer when the apex end contacts the surface of a container.
FIG. 6A is an enlarged cross sectional view of the apex end shown in FIG. 6
FIG. 6B is an enlarged bottom view of the apex end shown in FIG. 6A showing the pipette tips feet and collection channels.

As shown in FIG. 6 an alternative embodiment of pipette tip 55 is positioned within a tube or container 57 for the sample fluid 60. The tube 57 includes a relatively narrow open neck portion for receiving the pipette tip 55 and the pipetter barrel 48 with ejection sleeve 45. It is common in such instances that a slight lateral movement of the pipetter barrel 48 will cause the ejector sleeve 45 to contact and engage portions of the containers side wall 25. Such contact between the sleeve 45 and the sidewalls 25 of the container will transfer the sample fluid 60 and any contaminants to the sleeve 45 of the pipetter. Such fluid and contaminate can then be transferred to the next container or tube into which the pipetter and contaminated sleeve 45 is inserted producing unwanted cross contamination. To insure against such cross contamination, the outer surface of the pipetter including the sleeve 45 should be cleaned and possibly sterilized between each pipetting operation. As an alternative to this procedure, this new ergonomic pipette tip includes an additional tubular member 26 that extends upward about the sleeve 45 providing protection against such incidents.

The embodiment as shown in FIG. 6 is illustrated with optional membrane filter 50 that has been installed after the pipette tip 55 has been molded as in a secondary operation. The filter membrane 50 could be insert molded, die cut and/or laminated to a plastic ring 67 attached to the inner surface 128 of the lower portion 40 to maximize airflow either on its top, middle or bottom surface. If the filter 50 was very fragile, the ring 67 could be molded or laminated with small support ribs/openings across its surface. Although this is normally undesirable, some filter materials are more likely to tear or rip during installation and would require this addition support to help prevent this. After being manufactured separately, the filter ring 67 would then be installed and form a hermitic seal about its cylindrical or frustoconical outer surface whereby the flow of air would occur only through the Filter 50 and not between the filter ring's 67 outer surface and the inner surface 128 of the tip cavity 66 of the pipette tip 55.

It is also understood that prior art secondary plug filters could also be used for application that contamination between samples was not of the utmost concern. This secondary method of assembly would also be necessary for those applications where the inside tip cavity 66 of the pipette tip 55 would have a predetermined quantity of a dry reagent or reactant 61 deposited on its surface prior to the installation of the secondary filter 67 or other type of plug filters known in the arts. This would permit the introduction of a pre-introduced known quality of dried reagent or reactant 61 with a predetermined amount of sample fluid 60 into the pipette tip 55 allowing it to contact and mix to perform a particular diagnostic test or other reactions. This not only saves valuable time and additional vials or containers that are normally used for this purpose but more importantly uses all of the sample the pipette tip draws within its cavity since none is lost due to the transfer from one vial to another.

Referring to FIGS. 6A and 6B, the end of apex tip 55 has been modified with a improved embodiment to eliminate the potential plugging or clogging that can occur when a pipette tip contacts the inner surface of a container. Collection channels 27 are formed between the tip feet 28 of the apex end of pipette tip 55. They have the advantage of collecting the last remaining sample from container 57. This is because the discrete channels 27 are formed between the bottom of the container 57 and the feet 28 when the pipette tip contacts the container surface.

Figure 7:
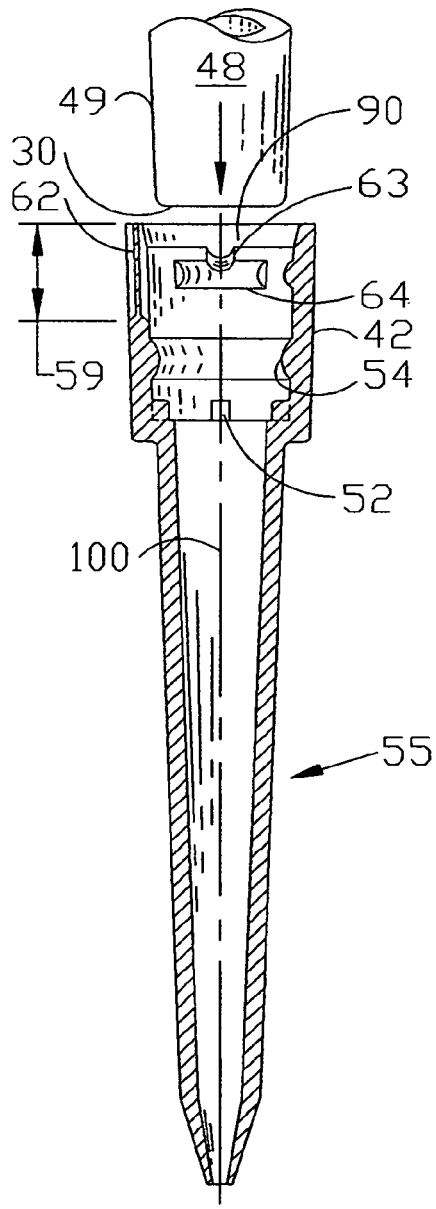
FIG. 7 is a cross section of a one material pipette tip embodiment that include expansion joints in its upper portion with optional annular rings and ribs for supporting and sealing the pipetter barrel.
Figure 7A:
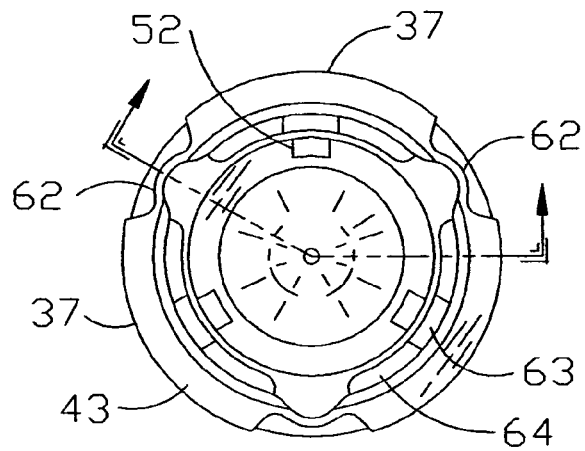
FIG. 7A shows a top view of FIG. 7 with expansion joints formed as living hinges in the relaxed or as-molded condition.
Figure 7B:
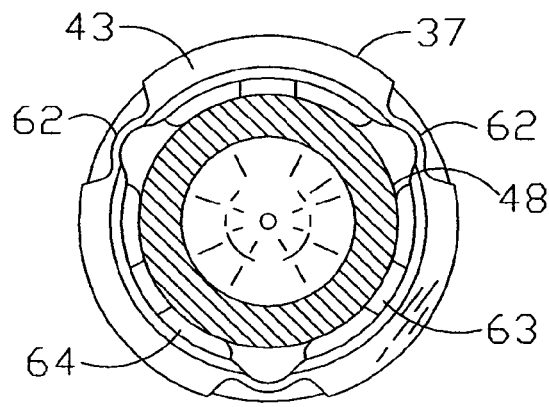
FIG. 7B shows a top view of FIG. 7 with a section view of the pipetter barrel as it begins entrance into the upper portion or the pipette tip.
Figure 7C:
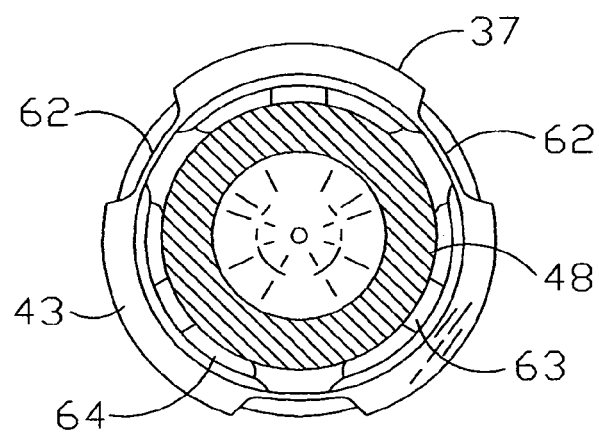
FIG. 7C shows a top view of FIG. 7 as if the pipetter barrel was engaged and the upper section expanded.

In an alternative embodiment to create an ergonomic design for easier tip insertion and ejection in either the two materials or preferred one material pipette tip, FIGS. 7, 8, 9, 10 and 11 are illustrated. This embodiment shown in one material employs the use of integral molded living hinge type expansion joints 62 to allow for the upper portion 42 to easily expand and contract without the problems of hoop stress associated with existing pipette tip. Each hinge 62 has a relaxed state having an arced configuration as shown in FIGS. 7A, 7B, and 8A, and an expanded state having a generally linear configuration as shown in FIGS. 7C and 8B. Insertion of the pipetter barrel 48 into the receiving cavity 90 of the upper portion 42 causes the hinges to expand stretching the hinge 62 from its arced form to a linear form. Living hinges are used particularly with polypropylene or polyethylene but can and do work with other polymers. Hinge or expansion joint 62 thickness varies but is usually between 0.008 to 0.018 inches. FIG. 7A shows a top view of FIG. 7 in the as-molded or relaxed condition prior to the installation of the pipetter barrel 48. The three living hinges joints 62 shown allow the cylindrical or frustoconical segmented wall sections 37 of upper portion 42 to easily expand when the pipetter barrel 48 is inserted into the upper portion 42 of pipette tip 55 as shown in FIG. 7B as it begins penetration and FIG. 7C when the pipetter barrel 48 has made seal with upper portion 45. The inherited design of the living hinge joint 62 eliminates the outward hoop stretching problems associated with prior art tips over the depth 59 that the living hinges 62 are molded as shown in FIG. 7. Within depth 59, optional vertical alignment or stabilizing ribs 63 can be added to the segmented wall sections 37 to help reduce friction and guide the pipetter barrel 48 into upper portion 42. In addition partial annular alignment or stabilizing rings 64 could also be added to these segmented wall sections 37 between the hinged expansion joints 62. It is also understood that one or more hinged expansion joint would also work in a similar manner as the 3 joints that are shown to describe this new invention.

As the pipetter barrel 48 penetrates beyond the depth 59 where they are no expansion joints 62, an optional annular sealing base ring 54 is shown. The seal is made when the pipetter barrel sealing surface 49 contacts and mates with sealing base ring 54 of the upper portion 42. At this point outward hoop stretching of the material does occur and a hermetic seal is made between these two parts. Such hoop stretching is minimized and only occurs in the area of sealing ring 54. This sealing surface could also be constructed with multiple sealing base rings 54 below the depth 59 with less interference to help reduce the friction between the pipetter and the upper portion 42. Also optional mechanical stops 52 are desired to limit vertical insertion depth of the distal end of pipetter barrel 48 into upper portion 42. This new ergonomic design allows for more controlled guiding and sealing of the pipetter barrel 48 to the pipette tip 55 while reducing the amount of axial force necessary for insertion and ejection of the Pipette Tip.

In another variation of the ergonomic pipette tip 55, FIG. 8 thru FIG. 9A show an alternative embodiment to create an ergonomic design for easier tip insertion and ejection. This embodiment shown in one material employs the use again of integral molded living hinge type expansion joints 62 to allow for the upper portion 42 to easily guide and expand and contract to the matting pipetter barrel 48. This more simple ergonomic design does not employ optional guide ribs or stabilizing rings as shown in prior embodiments. As the pipetter barrel 48 enters the upper portion 45 the sidewalls 49 of the pipetter barrel 48 mates with the segmented walls 37 of the upper portion 42. The hoop stress that is felt by the segmented wall 37 is directed outwardly to the tension developed within the expansion joints 62 as the pipetter barrel 48 is controlled and guided downward towards the sealing zone. As the pipetter penetrates further, as shown by the dashed lines in FIG. 9A the pipetter barrel 48 contacts and easily expands the optional thin walled sealing base zone 44 making a hermetic seal. This thin wall 65 section can be reduced to 0.010 to 0.025 to help minimize hoop stress problems associated with prior art in the seal matting area. In addition optional outside mounting ribs 38 are used as stops to prevent the pipette tips from jamming into the mounting hole racks when the pipetter barrel 48 is installed into the upper portion 42 of the pipette tip.

FIG. 10 illustrates a multichannel pipetter 32 with 6 individual pipetter barrels 48 ready to being installed into the strip of the new one-piece, one-material multichannel ergonomic pipette tips 56. These pipette tips include the living hinge expansion joints 62 as shown in FIG. 9, 9A and are connected on centers to the multichannel pipetter barrels 48. It is a one piece ergonomic design that replaces 6 independent pipette tips and offers easier installation, less independent rocking, lower cost and easier removal than prior art tips.

FIG. 11 illustrates a standard pipetter 33 shown ready to be installed onto to a one-piece, one material ergonomic pipette tip upper portion 42 that is constructed using expansion joints 62 as shown in FIGS. 9 and 9A. The lower portion is constructed with one or more lower portions 40 with or without optional filters similar in function as that of FIG. 4.

Figures 12, 13, 14:
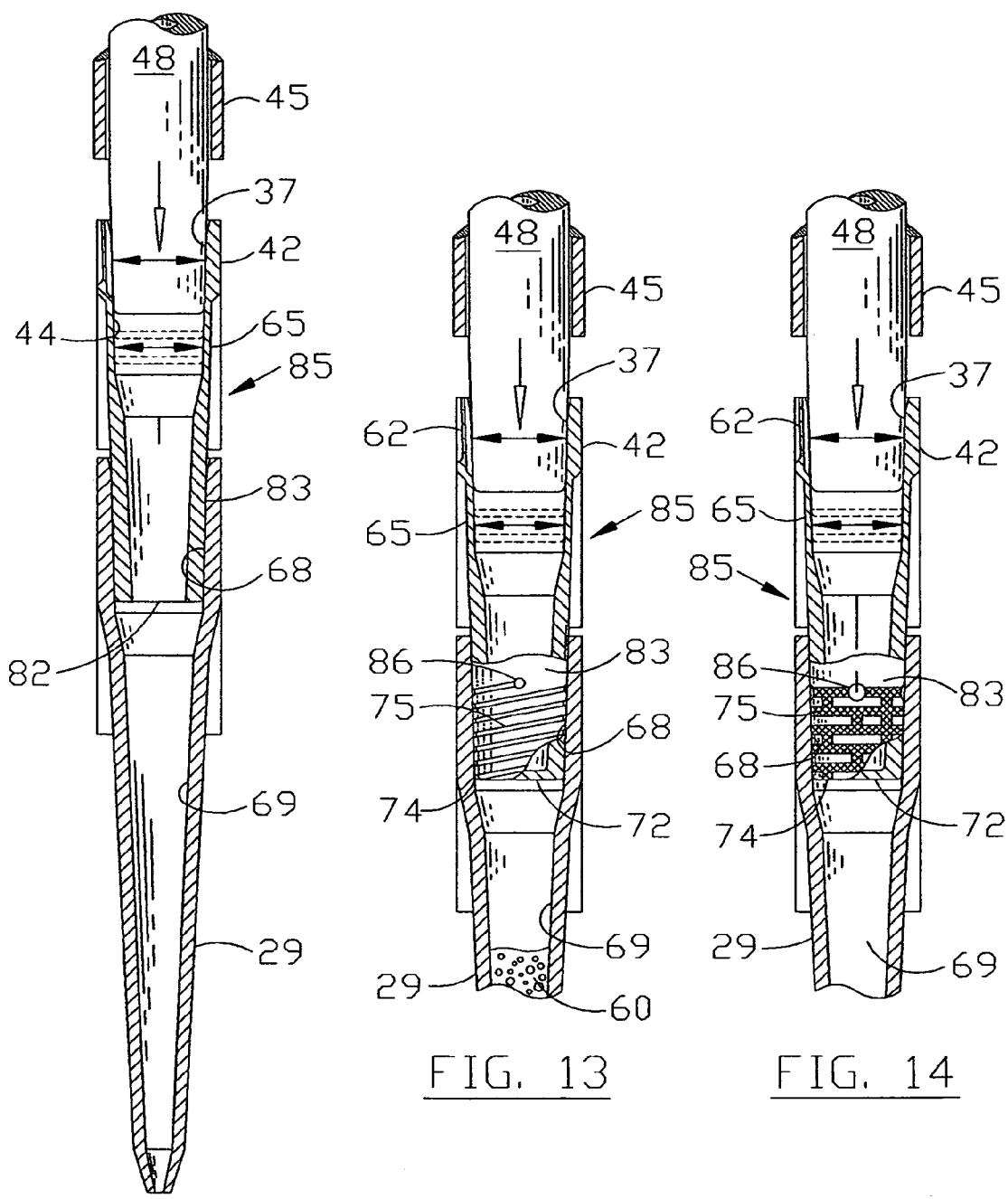
FIG. 12 is cross section view of an ergonomic pipetter adapter showing the pipetter barrel being guided and expanding the joints in its uppermost portion. As the pipetter penetrates further, as shown by the dashed lines, it contacts and easily expands the optional thin walled sealing zone making a hermetic seal. The adapter is also shown installed into a cross section detail of a standard pipette tip.
FIG. 13 is a cross section of an alternative ergonomic adapter embodiment whereby the central hole has been eliminated and inner vent channels have been added on the adapters outer-surface to provide aerosol free air to the pipetter.
FIG. 14 is a cross section of an alternative ergonomic adapter embodiment whereby the central hole has been eliminated and textured vent channels have been added on the adapters outer-surface to provide aerosol free air to the pipetter.

FIGS. 12, 13 and 14 illustrate a new ergonomic barrel adapter 85 that is adapted to fit between a standard pipette tip 55 and the pipetter barrel 48 of a pipetter. One embodiment is shown in FIG. 12 whereas the adapter 85 is an open-end configuration that can be use with an optional filter membrane 50 (not shown) or filter plug. The upper portion 42 is similar in function as the upper portion 42 shown and described in FIG. 9A and employs the use again of the integral molded living hinge type expansion joints 62 to allow for the upper portion 42 to easily guide and expand about the pipetter barrel 48. The barrel adapter 85 in this embodiment is constructed to hermetically seal surface 83 to the inside surface 68 of standard pipette tip 55. When suction is applied from the pipetter through the pipetter barrel 48, the air is drawn from the pipette tip cavity 69 into the open end 82 of the barrel adapter 85, though the barrel 48 and into the Pipetter.

FIG. 13 shows another embodiment where the barrel adapter 85 is a cup-shaped hollow member with a closed end 72 that is molded with small filtering channels 75 on its outside sealing surface 83. These small filtering channels 75 create an air path between the inside sealing surface 68 of the standard pipette 29 and the barrel adapter outer sealing surface 83. One or more air path begin at leak path 74 inside the pipette tip cavity 69. The air follows about the circular path until it reaches one or more openings 86 that provide a passageway into the hollow barrel adapter 85 allowing access in through the pipetter barrel 48 and into the pipetter. This long and very small air path inhibits the aerosol and contaminates from the fluid 60 that has been aspirated into standard pipette tip 29 from the pipetter.

FIG. 14 is a similar embodiment as FIG. 13 except the air path is constructed from a maze of very small textured surfaces creating similar filtering channels 75. It is understood other filtering configuration (ie: 0001 to 0.0050 inch) may work assuming they have at least one entry point 74 on the closed end 72 of the adapter 85 and at least one exit hole 86 through the adapter 85 to a suction device such as a pipetter.

Figure 15:
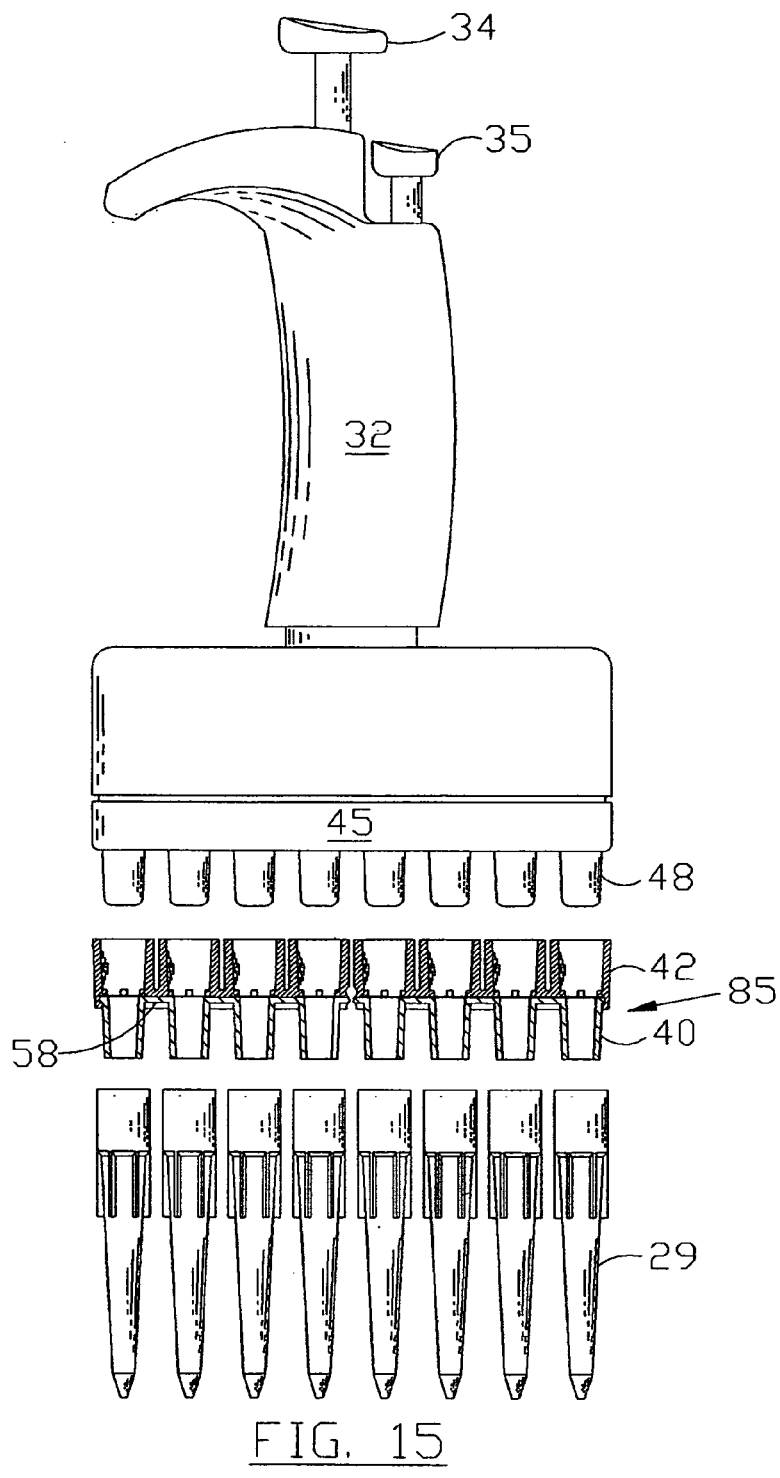
FIG. 15 is a cross section of a two material ergonomic adapter shown with optional filter membranes being injection molded together with a thin optional connecting rib to facilitate handling. The adapter is shown prior to being installed between a multichannel pipetter and 8 standard pipette tips.

FIG. 15 illustrates the two material ergonomic barrel adapter 85 being molded together to adapt to a standard 8 channel pipetter similar to those manufactured by Oxford, Brinkman, Eppendorf etc. These multichannel pipetters work very similar to the single channel version with the exception that it will pick up 4, 6, 8, 10, 12 etc. individual pipette tips at one time. This new ergonomic pipetter adapter strip 73 shows 8 of the new improved ergonomic barrel adapters 85 molded in a one-piece configuration by means of a thin rib 58. This embodiment allows the manufacturer to mold the multichannel strip adapters 73 for easier handling and at a lower cost. This embodiment would also allow for the use of an optional pre-cut filter strip membrane 50 containing the desired number of filter membrane disc connected by a thin web of filter material for easier handling during the insert molding cycle of the 2, 4, 6, 8 or any combination of ergonomic adapters 85 at one time. The upper portion 42 would be manufactured from an elastic material as discussed previously in FIG. 2, 2A and FIG. 3. The lower portion would be from a second material again as discuss previously.

Figure 16:
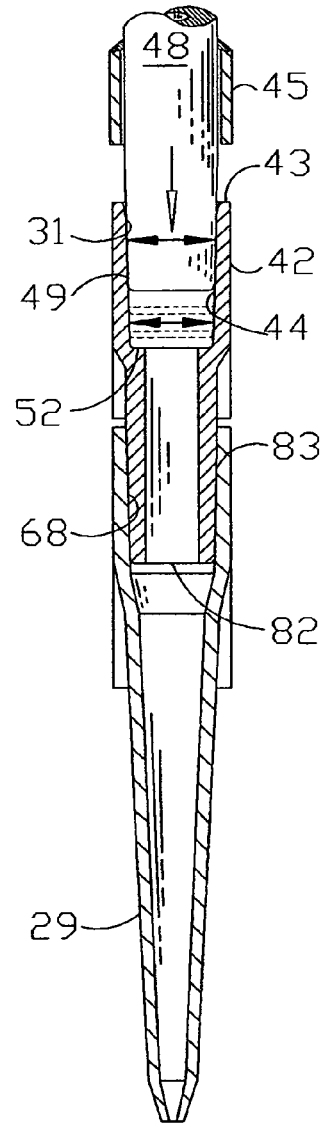
FIG. 16 illustrates an enlarged cross sectional view of an ergonomic adapter constructed from an elastic material. The pipetter barrel is shown being guided by the resilient adapter surfaces and easily expanding its uppermost portion. As the pipetter penetrates further, as shown by the dashed lines, it contacts and expands the sealing zone making a hermetic seal. The adapter is also shown installed into a cross section detail of a standard pipette tip. The adapter may include an optional filter membrane.

FIGS. 16, 17, 18 and 19 each illustrate a one piece, one material new ergonomic barrel adapter. In this embodiment the entire adapter 85 may be molded from elastic or flexible material as previously described in FIGS. 1 through 4 and will offer the same ergonomic advantages over the prior art. This variation however, will in some instances require a chemical resistant elastomer and may not be able to be colored depending on the sample materials that may come in contact with the adapter 85. FIG. 16 shows a standard pipetter barrel 48 being installed into the elastic rubber-like ergonomic adapter. As the pipetter barrel 48 enters the upper portion 42 the sidewalls 49 of the pipetter barrel 48 mate with the inside walls 31 of the upper portion 42. The hoop stress that is felt by the walls is minimal due to the elastic nature of the material. As the pipetter barrel 48 is controlled and guided downward towards the sealing zone 44 as shown by the dashed lines, the pipetter barrel 48 contacts and easily expands the resilient sealing zone 44 making a hermetic seal. The one-piece design offers resilient sealing capability not only between the pipetter barrel 48 and upper portion 42 as just described but also between the sealing surface 83 and the inside tip cavity 68 of pipette tip 29. This low cost design can also be constructed with optional filter membrane 50 (not shown) or plug filter mounted on the open end 82 or annulus 52 or anywhere between.

Figure 17:
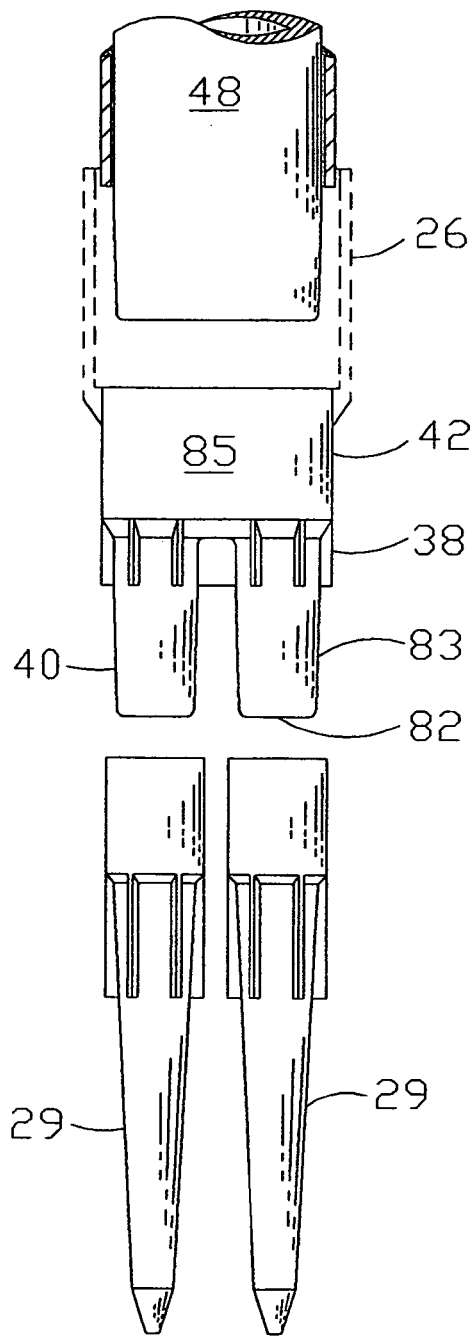
FIG. 17 illustrates a standard use pipetter ready to be installed into an alternative one-piece elastic ergonomic adapter. The upper portion of the adapter is shown with an optional contaminator protector in dashed lines. The lower portion integral with the upper portion, with or without filters, shows a minimum of two conical receiving bosses for attachment of standard pipette tips.
Figure 18:
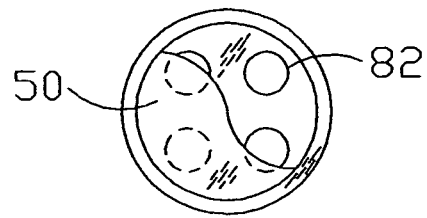
FIG. 18 illustrates a top view of FIG. 17 with 4 openings for attachment of pipette tips with optional membrane filter being cut-away to show inside detail of adapter.
Figure 19:
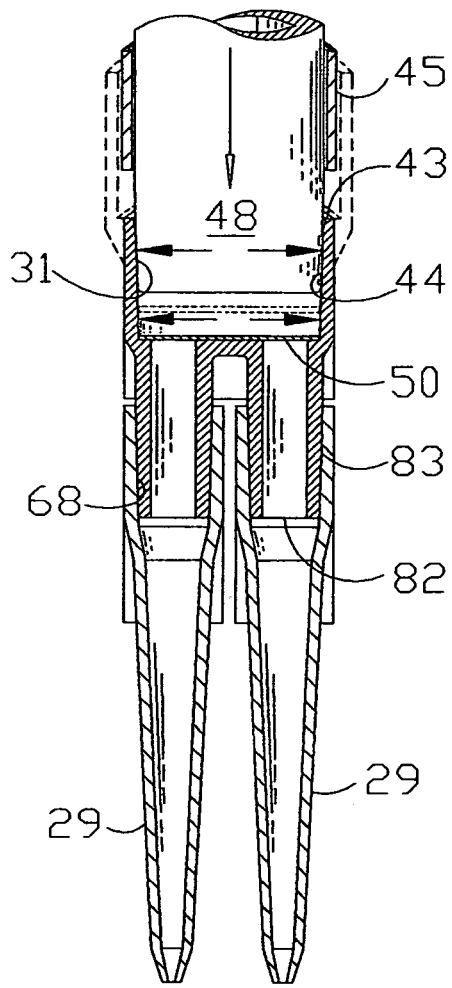
FIG. 19 is a cross sectional view of FIG. 17 with the pipetter barrel being guided by the resilient adapter surfaces and easily expanding its uppermost portion. As the pipetter penetrates further, as shown by the dashed lines, it contacts and easily expands the sealing zone making a hermetic seal. The adapter is also shown installed into a cross sectional detail of a minimum of 2 standard pipette tips.

FIGS. 17 and 19 illustrate a standard pipetter barrel 48 shown being installed into the upper portion 42 of barrel adapter 85 similar to FIG. 16. The upper portion in this embodiment is connected to one or more lower portion 40 allowing the barrel adapter 85 to be installed onto one or more standard pipette tips. This becomes very beneficial when a large number of dispensing must be made and is especially useful when working with well plates and the like. FIG. 18 is a top view of the adapter showing lower portion 40 being covered by the optional filter membrane 50. In addition the adapter 85 may also include a contaminator protector 26 as shown in dashed lies in FIG. 17.

As the samples become smaller, more testing is required and the tray wells continue to increase from say the standard 96 well plate to the 384 and again to 1536, there exist a real need to accommodate this growth with new and innovative products such that are described throughout this patent.

BRIEF DESCRIPTION OF NUMBERED PARTS

25. Container sidewall
26. Contamination protector
27. Collection channels—apex end
28. Pipette tip feet—apex end
29. Standard pipette tip
30. Distal end of pipetter barrel 48
31. Resilient guide surface—upper portion 42
32. Multichannel pipetter
33. Standard pipetter
34. Push button—pipetter
35. Push button—ejector
36. Alignment rings—upper portion
37. Segmented wall sections—upper portion
38. Mounting ribs—pipette tip
39. Tip cavities
40. Lower portion
41. Tubular member—molded or secondary plastic, metal or glass tubing
42. Upper portion
43. Top Surface—upper portion
44. Sealing base zone—upper portion
45. Ejector sleeve
46. Apex end-angled pipette tip
47. Septum or cap to puncture
48. Pipetter barrel
49. Pipetter barrel sealing surface
50. Filter membrane for sterile air or plug filter
51. Interface or mechanical seal between upper portion and lower portion
52. Mechanical stop for pipetter barrel 48
53. Angled surface or lead-In for upper portion
54. Sealing base rings—upper portion
55. Ergonomic Pipette Tip
56. Ergonomic multichannel pipette tips
57. Container or tube
58. Multichannel pipette tip connecting ribs
59. Depth of living hinge type expansion joints
60. Fluid (Sample)
61. Predetermined amount of dry reagent/reactant
62. Living hinge type expansion joint
63. Vertical alignment and or stabilizing rib—upper portion
64. Annular alignment or stabilizing rings—Segmented
65. Thin Wall
66. Inside tip cavity
67. Filter ring for holding filter media
68. Sealing surface—standard pipette tip
69. Pipette Tip Cavity
70. Pipette Tip Outer Surface
No. 72 Closed end of adapter
74. Lead path entry or exit
75. Small filtering venting channels
78. Apex end
82. Open end—barrel adapter
83. Sealing surface—barrel adapter
85. Barrel adapter—overall
No. 86 Exit hole through adapter
90. Central receiving cavity
92. Perimeter ledge Inner Portion—Stop—Lower Portion
94. Top Face—Lower portion
96. Inside bottom edge portion—Upper portion
98. Bottom face of bottom edge—Upper portion
100. Longitudinal Axis
102. Inward facing surface—Upper portion
104. Upper edge portion—Lower portion
108. Outward facing surface—Lower portion
110. Tunnel-shaped aperture—Lower portion
112. Main body—Lower portion
114. Top Lip—Lower portion
116. Lower face of mechanical stop—Upper portion
118. Upward facing surface of flange 120—Upper portion
120. Inward facing flange—Upper portion
124. Uppermost entry region—Upper portion
126. Upper surface of stop 52—Upper portion
128. Inner surface—Lower portion

What is claimed:

1. A pipette tip comprising:
   an upper portion for attachment to a barrel of a pipetter in a fluid tight relationship, said upper portion having an interior frustum shaped cavity and at least one flexible expansion joint allowing radial expansion of said upper portion upon penetration of the pipetter barrel into said cavity, and
   a lower portion including an apex end for receiving a predetermined volume of fluid, said apex end including a plurality of discrete feet, said discrete feet defining channels therebetween for drawing a predetermined volume of fluid through said channels while said apex end of said pipette tip is contiguous with the bottom of a container holding said fluid.

2. The pipette tip of claim 1, further including a particulate air filter for passing particulate free air to said pipetter is located between said upper portion and said predetermined volume of fluid.

3. The pipette tip of claim 1 wherein said rigid lower portion has an inside surface and is coated with a predetermined amount of reagent or reactant to mix with said predetermined volume of fluid.

4. A pipette tip comprising:
   an upper portion for attachment to a barrel of a pipetter in a fluid tight relationship, said upper portion including an interior frustum shaped cavity,
      at least one axial spaced wall section of a first thickness and having axial ends in a circumferential direction of the upper portion,
      at least one flexible expansion joint of a second thickness, thinner than the first thickness, which defines at least one recess between said axial ends,
   wherein said at least one axial spaced wall section and said at least one flexible expansion joint are engaged along the circumferential direction of the upper portion to define a circumference of the upper portion,
   wherein said at least one flexible expansion joint expands along the circumferential direction of the upper portion between the axial ends of said at least one wall section to allow radial expansion of said upper portion upon penetration of the pipetter barrel into said cavity, and
   at least one lower portion including an apex end for receiving a predetermined volume of fluid.

5. The pipette tip of claim 4, further including a particulate air filter for passing particulate free air to said pipetter is located between said upper portion and said predetermined volume of fluid.

6. The pipette tip of claim 4 wherein said at least one flexible expansion joint is a plurality of flexible expansion joints and said at least one wall section is a plurality of axially spaced wall sections,
   wherein said axially spaced wall sections are spaced apart from each other by, and also connected by, the flexible expansion joints which are positioned between said axially spaced wall sections.

7. The pipette tip of claim 4, wherein said upper portion includes means for insuring uniformed depth of penetration of said pipetter barrel into a base said pipette tip to maintain a uniform pipette tip interference between said base and said pipetter barrel as successive pipette tips are mounted on and ejected from said pipetter barrel.

8. The pipette tip of claim 4, wherein said at least one axial wall section has a length that is longer along a circumferential direction of the upper portion than said at least one flexible joint when the upper portion is not expanded.

9. The pipette tip of claim 4, wherein said flexible expansion joint has a relaxed state having an arched configuration and an expanded state having a general linear configuration.

10. The pipette tip of claim 4 wherein said upper portion includes segmented axially spaced and mating annular cylindrical support ribs.

11. The pipette tip of claim 4 wherein said upper portion also includes a sealing region of predetermined length in the lowermost portion of said upper portion between said expansion joint and said lower portion, said sealing region being sufficiently thin that said sealing region will expand slightly to form an interference fit between said sealing region and said barrel of a pipetter.

12. The pipette tip of claim 4 wherein said apex end includes means for receiving said predetermined volume of fluid when said apex end is contiguous with a container bottom.

13. The pipette tip of claim 4 wherein said lower portion has an inside surface and is coated with a predetermined amount of reagent or reactant to mix with said predetermined volume of fluid.

* * * * *